(12) United States Patent
Kita et al.

(10) Patent No.: US 8,475,044 B2
(45) Date of Patent: Jul. 2, 2013

(54) ANALYZING APPARATUS

(75) Inventors: Hiroaki Kita, Takatsuki (JP); Tatsuya Inoue, Takatsuki (JP); Hiroyuki Kawakami, Takatsuki (JP)

(73) Assignee: Rigaku Corporation, Tokyo (JP)

( * ) Notice: Subject to any disclaimer, the term of this patent is extended or adjusted under 35 U.S.C. 154(b) by 96 days.

(21) Appl. No.: 13/268,006

(22) Filed: Oct. 7, 2011

(65) Prior Publication Data

US 2012/0093299 A1 Apr. 19, 2012

(30) Foreign Application Priority Data

Oct. 14, 2010 (JP) ................. 2010-231299

(51) Int. Cl.
*H05G 1/00* (2006.01)
(52) U.S. Cl.
USPC .......................... 378/208; 378/44
(58) Field of Classification Search
USPC .................. 378/44–46, 58, 62, 208
See application file for complete search history.

(56) References Cited

U.S. PATENT DOCUMENTS 6,166,505 A 12/2000 Sato

FOREIGN PATENT DOCUMENTS

| JP | 54-029828 Y2 | 9/1979 |
|---|---|---|
| JP | 61097087 A | 5/1986 |
| JP | 02024581 A | 1/1990 |
| JP | 03156338 A | 7/1991 |
| JP | 03274747 A | 12/1991 |
| JP | 08-184573 A | 7/1996 |
| JP | 11345001 A | 12/1999 |
| JP | 11354405 A | 12/1999 |
| JP | 2008004581 A | 1/2008 |
| JP | 2010157639 A | 7/2010 |

OTHER PUBLICATIONS

Japanese Office Action dated Mar. 21, 2012; Application No. 2010-231299.

*Primary Examiner* — Courtney Thomas
(74) *Attorney, Agent, or Firm* — Sughrue Mion, PLLC

(57) ABSTRACT

An analyzing apparatus of the present invention includes a cassette unit (20) for generating a cassette identification signal identifying a type of a cassette (21), a sample holder (8) having an insertion hole (83) and a ring shaped pedestal (82), a transport section (23) for transporting the sample (S), a sample holder identifying section (35) for generating a sample holder identification signal identifying the type of the sample holder appropriate to the diameter of the sample to be placed, and a determining section (40) for determining, based on the cassette identification signal and the sample holder identification signal, whether or not the diameter of the sample to be accommodated in the cassette (21) and the diameter of the sample to be placed on the pedestal of the sample holder (8) match with each other.

12 Claims, 16 Drawing Sheets

ANALYZING APPARATUS

CROSS REFERENCE TO THE RELATED APPLICATION

This application is based on and claims Convention priority to Japanese patent application No. 2010-231299, filed Oct. 14, 2010, the entire disclosure of which is herein incorporated by reference as a part of this application.

BACKGROUND OF THE INVENTION

1. Field of the Invention

The present invention relates to an apparatus for analyzing a disc shaped sample to be analyzed such as, for example, a semiconductor wafer or magnetic disc and, more particularly, to a device used in such analyzing apparatus for identifying a sample holder for holding the sample to be analyzed.

2. Description of Related Art

In the analyzing apparatus such as, for example, the X-ray analyzer, a variety of sample holders having dimensions and/or shapes that differ from each other according to types of the sample to be analyzed have hitherto been employed in order for samples of various sizes and/or shapes to be analyzed. If the sample holder that does not suit to the particular sample type is used, a problem has been recognized that one or both of the sample and the analyzer are often contaminated and/or the use of the unsuitable sample holder leads to a trouble in the analyzer. Accordingly, the patent document 1 listed below discloses an X-ray fluorescence spectrometer in which a read-out head is arranged in face-to-face relation with a side face of a cylindrical sample container accommodating therein the sample to be analyzed and an indicium such as, for example, a sample identification label and/or an analytical condition specifying label is applied to the side surface of the sample container so that the analyzing apparatus can be controlled in dependence on the result of reading performed by the read-out head.

The patent document 2 listed below disclosed an X-ray analyzing apparatus designed to measure a sample, held by sample holder of a type in which a mask having defined therein a hole of a size (mask size) appropriate to the size of the sample is selectively fitted to the top of the sample to allow a measuring area of the sample to be exposed through such hole. According to the patent document 2, at least a surface of the mask is prepared from a material containing a specific element, the content of which in the sample is minute or zero and which is of a kind differing in dependent on the size of the mask size, so that the mask size can be determined by measuring the intensity of secondary X-rays emanating from the specific element.

Prior Art Literature

[Patent Document 1] JP Laid-open Utility Model Publication No. S54-29828

[Patent Document 2] JP Laid-open Patent Publication No. H08-184573

It has, however, been found that the prior art analyzing apparatuses discussed above have some problems as described below.

In the X-ray fluorescence spectrometer disclosed in the patent document 1 referred to above, the sample to be analyzed is accommodated within a sample container and an indicium such as, for example, a sample identification label and/or an analytical condition specifying label is applied to the sample container. Accordingly, it is impossible to identify the sample container before the sample is placed within such sample container, and, hence, the indicium such as, for example, the sample identification label and/or the analytical condition specifying label must be applied for each of the sample container.

On the other hand, according to the mask size determining method disclosed in the patent document 2 discussed above, the mask is made of the material containing the specific element, the content of which in the sample is minute or zero and which is of a kind differing in dependent on the size of the mask size, followed by irradiation with primary X-rays so that the intensity of the secondary X-rays emanating from the specific element can be measured to determine the mask size. Accordingly, since the use of the mask prepared from the specific element is essential and, also, since the sample holder need be transported to a measuring site, where the sample holder is irradiated with the primary X-rays for the determination of the mask size, an extra amount of time is required.

SUMMARY OF THE INVENTION

In view of the foregoing problems and inconveniences inherent in the prior art X-ray analyzing apparatuses, the present invention has for its object to provide an X-ray analyzing apparatus of a type, which requires neither the indicium such as the sample identification label nor the mask prepared from the specific element and in which the sample holder can be automatically identified in a matter of minutes before the sample is transported to the sample holder.

In order to accomplish the foregoing object of the present invention, the present invention in accordance with a first aspect thereof provides an analyzing apparatus for analyzing a disc shaped sample, which includes a cassette unit comprising a cassette for accommodating the sample and a cassette identifying section for identifying a type of the cassette and then generating a cassette identification signal descriptive of the diameter of the sample to be accommodated; a sample holder having defined therein an insertion hole with a diameter, corresponding to the diameter of the sample, and through which the sample is inserted from above and including a ring shaped pedestal on which the sample is placed; a transport section for transporting the sample from the cassette onto the sample holder; a sample stage on which the sample holder is placed; a sample holder identifying section for detecting a radially oriented end of the insertion hole in the sample holder or a radially inward end of the ring shaped pedestal and then generating a sample holder identification signal for identifying the type of the sample holder that corresponds to the diameter of the sample to be placed; and a determining section for determining whether or not the diameter of the sample to be accommodated in the cassette and the diameter of the sample to be placed on the pedestal of the sample holder match with each other, based on the cassette identification signal, generated from the cassette identifying section, and the sample holder identification signal generated from the sample holder identifying section.

In the analyzing apparatus of the structure described above, in the event that the determining section determines that the diameter of the sample to be accommodated in the cassette and the diameter of the sample to be placed on the pedestal of the sample holder match with each other, the transport section transports the sample from the cassette onto the sample holder placed on the sample stage.

According to the first aspect of the present invention described above, since it is possible to automatically identify the sample holder by detection of the radially oriented end of the insertion hole in the sample holder or the radially inward end of the ring shaped pedestal and then to automatically determine whether or not the diameter of the sample to be accommodated in the cassette and the diameter of the sample to be placed on the pedestal of the sample holder match with each other, the use of the indicia such as, for example, the sample identification label and/or the mask prepared from the specific element is not needed and the sample holder can be automatically identified in a matter of minutes before the sample is transported to the sample holder.

The present invention in accordance with a second aspect thereof also provides an analyzing apparatus for analyzing a disc shaped sample, which includes a cassette unit comprising a cassette for accommodating the sample and a cassette identifying section for identifying a type of the cassette and then generating a cassette identification signal descriptive of the diameter of the sample to be accommodated; a sample holder having defined therein an insertion hole with a diameter, corresponding to the diameter of the sample, and through which the sample is inserted from above and including a ring shaped pedestal on which the sample is placed; a transport section for transporting the sample from the cassette onto the sample holder; a sample stage on which the sample holder is placed; a sample holder identifying section for detecting a radially oriented end of the insertion hole in the sample holder and then generating a sample holder identification signal for identifying the type of the sample holder that corresponds to the diameter of the sample to be placed; and a determining section for determining whether or not the diameter of the sample to be accommodated in the cassette and the diameter of the sample to be placed on the pedestal of the sample holder match with each other, based on the cassette identification signal, generated from the cassette identifying section, and the sample holder identification signal generated from the sample holder identifying section; in which in the event that the determining section determines that the diameter of the sample to be accommodated in the cassette and the diameter of the sample to be placed on the pedestal of the sample holder match with each other, the transport section transports the sample from the cassette onto the sample holder placed on the sample stage.

According to the second aspect of the present invention described above, since it is possible to automatically identify the sample holder by detection of the radially oriented end of the insertion hole in the sample holder and then to automatically determine whether or not the diameter of the sample to be accommodated in the cassette and the diameter of the sample to be placed on the pedestal of the sample holder match with each other, effects similar to those afforded by the analyzing apparatus according to the previously described first aspect of the present invention can be obtained.

The sample holder employed in the analyzing apparatus according to the second aspect of the present invention described above preferably has a recessed inlet of a round configuration defined in the disc shaped pedestal and in which the sample holder identifying section detects a radially oriented end of the insertion hole in the sample holder or a radially oriented end of the recessed inlet and then generates the sample holder identification signal for identifying the type of the sample holder that corresponds to the diameter of the sample to be placed. Even in this case, effects similar to those afforded by the analyzing apparatus according to the previously described first aspect of the present invention can be obtained.

The analyzing apparatus according to any one of the first and second aspects of the present invention may include a sample holder replacement door which is selectively opened or closed at the time of replacement of the sample holder, so that the sample holder can retain the sample holder identification signal when the sample holder replacement door is closed, but invalidating the sample holder identification signal when the sample holder replacement door is opened. In such case, while once the sample holder replacement door is switched from a closed condition to an opened condition, it will become uncertain whether or not the sample holder has been replaced, it is possible to ensure the sample holder identification if the sample holder identification signal is invalidated and the sample holder identification is then again carried out.

In the analyzing apparatus according to any one of the first and second aspects of the present invention, the sample holder identifying section, when the sample holder replacement door is closed, preferably identifies the type of the sample holder and then generates the sample holder identification signal. In this case, since the type of the sample holder is identified while the sample holder replacement door is closed, the safety during the operation brought about by the movement of the sample stage can be ensured.

In the analyzing apparatus according to any one of the first and second aspects of the present invention, the sample holder replacement door is preferably operated in the sequence in which the sampler holder replacement door is released from a locked condition by a lock release switch for unlocking a locking mechanism, opened by an analyst, invalidates the sample holder identification signal then retained, closed by the analyst, locked by the lock mechanism, and retains the sample holder identification signal generated by the sample holder identifying section. In such case, since the sample holder replacement door is actuated in the sequence of identifying the type of the sample holder, when the sample holder replacement door having been closed is again locked, and then retains the sample holder identification signal, not only can the reliable sample holder identification be accomplished, but also the safety during the operation brought about by the movement of the sample stage can be ensured.

In the analyzing apparatus according to any one of the first and second aspects of the present invention, the sample holder identifying section may include a non-contact type sensor assembly for detecting at least one of the radially oriented end of the insertion hole, the radially inward end of the ring shaped pedestal and a radially oriented end of the recessed inlet and operable to detect the presence or absence of the sample within the sample holder placed on the sample stage and then generating a sample presence or absence signal. In such case, since the presence or absence of the sample within the sample holder can be detected, initiation of the identifying operation of the sample holder in a condition with the sample placed in the sample holder can be prevented and the sample holder identification can be made reliable.

The analyzing apparatus according to any one of the first and second aspects of the present invention may furthermore include a manual loading mode in which an analyst places the sample in the sample holder then placed on the sample stage and then moves the sample stage from a loading position, which is a position where the sample is placed, to a measuring position, which is a position where the sample is measured, for measurement of the sample. In this case, measurement can be accomplished by manually loading the sample, which cannot be accommodated within the cassette, or a sample other than the sample accommodated within the cassette.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DESCRIPTION OF THE PREFERRED EMBODIMENTS

Figure 1:
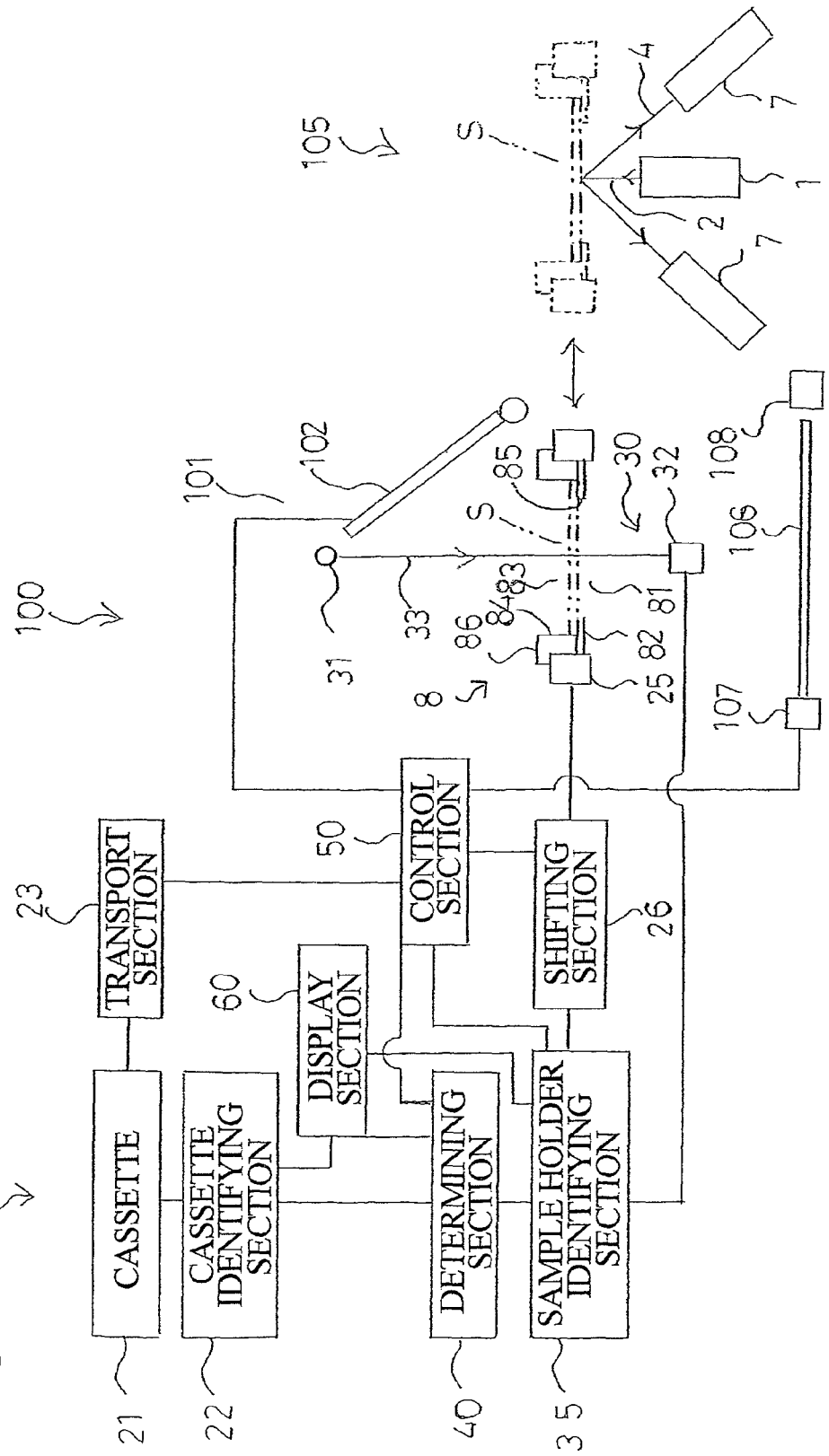
FIG. 1 is a schematic diagram showing an X-ray analyzing apparatus according to a first preferred embodiment of the present invention.

Hereinafter, an analyzing apparatus such as, for example, an X-ray analyzing apparatus according to a first preferred embodiment of the present invention will be described in detail. By way of example, the description will be made with reference to the accompanying drawings in connection with the structure of the X-ray analyzing apparatus, which is an X-ray fluorescence spectrometer for analyzing a disc shaped sample. As shown in FIG. 1, the X-ray analyzing apparatus includes a cassette unit 20 which is made up of a cassette 21 for accommodating therein a disc shaped sample S such as, for example, a wafer or a magnetic disc and a cassette identifying section 22 for identifying a type of the cassette 21 and then transmitting a cassette identification signal corresponding to the diameter of the sample S to be accommodated, a main body 100 of the X-ray fluorescence spectrometer, and a transport section 23 such as, for example, a robot for transporting the sample S from the cassette 21 to the main body 100 of the X-ray fluorescence spectrometer.

For accommodating a particular sample S, one of the cassettes 21 that suits to respective samples S of 100, 125, 150 and 200 mm in diameter is employed, and the cassette identifying section 22 includes a disposition site where the selected cassette 21 is disposed, a detecting unit, for example, a transmissive type photo-sensor assembly (not shown) provided at a position corresponding to a particular type of the cassette 21 at the disposition site, and is operable to identify the selected cassette 21. When the cassette 21 is placed on the cassette identifying section 22, the cassette identifying section 22 identifies the type of the cassette 21 and then transmits a cassette identification signal descriptive of the diameter of the sample S to be accommodated within such identified cassette 21 with such cassette identification signal subsequently retained therein. The detecting unit used to identify the cassette 21 may not necessarily be limited to the transmissive type photo-sensor assembly, but may be employed in the form of another non-contact sensor such as, for example, a reflective type photo-sensor assembly or an electric capacitance sensor, or a contact type sensor such as a microswitch.

Figure 2:
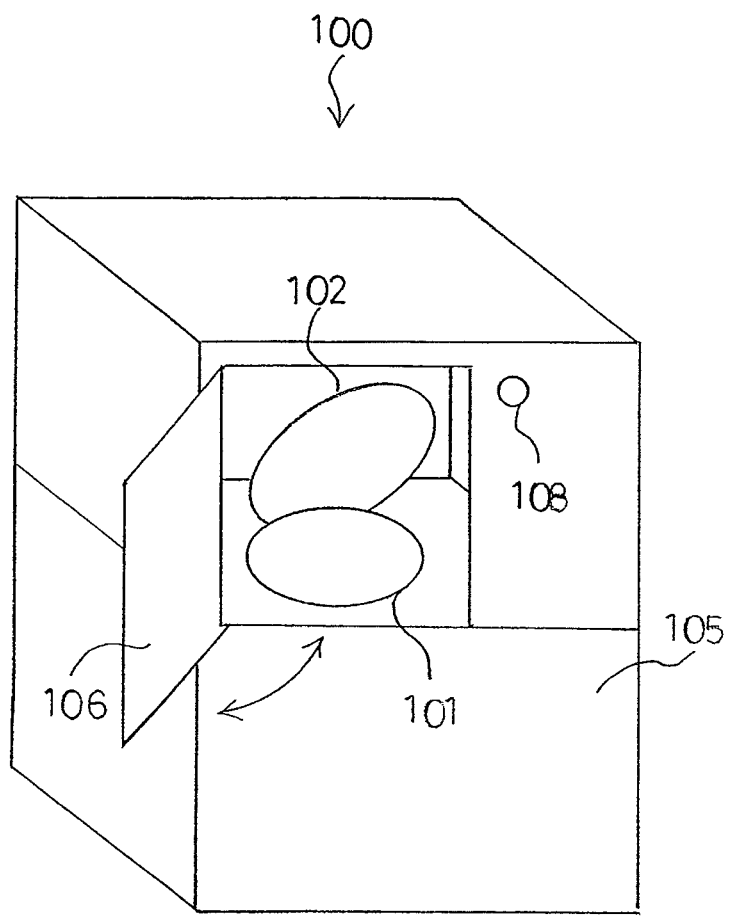
FIG. 2 is a schematic diagram showing an outer appearance of a main body of the X-ray analyzing apparatus.

As shown in FIG. 2 showing the outer appearance of the main body 100, the main body 100 includes a sample loading unit 101 for loading the sample S (best shown in FIG. 1), transported from the cassette 21 (best shown in FIG. 1) by the transport section 23 and placing it on a sample holder 8 as best shown in FIG. 1, an analyzing chamber 105 for analyzing the sample (best shown in FIG. 1) placed on the sample holder 8 (best shown in FIG. 1), and a sample holder replacement door 106 that is selective opened or closed at the time of replacement of the sample holder 8 (as best shown in FIG. 1). The sample loading unit 101 has a lid 102 for opening or closing the sample loading unit 101 from above, and the sample holder replacement door 106 is locked by a locking mechanism 107 (best shown in FIG. 1) when the sample holder replacement door 106 is in a closed condition and is released by a lock release switch 108.

As best shown in FIG. 1, the main body 100 also includes a sample holder (shown in FIGS. 3A and 3B), having defined therein an insertion hole 83 of a diameter corresponding to the diameter of the sample S and through which the sample S is inserted and a ring shaped pedestal 82 on which the sample S is placed, a sample stage 25 for supporting thereon the sample holder 8, a shifting section 26 for moving the sample stage 25 in a direction radially of a hole 81 defined in the pedestal of the sample holder 8, and a sample holder identifying section 35 for detecting a radially inward end 85 of the ring shaped pedestal 82 of the sample holder to transmit a sample holder identification signal for identifying a type of the sample holder 8 corresponding to the diameter of the sample S to be placed. The sample holder identifying section 35 has a transmissive type photo-sensor assembly 30. This transmissive type photo-sensor assembly 30 is made up of a light source 31 for projecting a light beam in a direction axially of the hole 81 in the pedestal of the sample holder and a light-sensitive detector 32 for detecting the beam having passed through the hole 81 in the pedestal and is capable of transmitting a light presence or absence signal indicative of the presence or absence of whether the light-sensitive detector 32 has received light. The light source 31 of the transmissive type photo-sensor assembly 30 is fitted to an apparatus housing above, for example, the lid 102 and the light-sensitive detector 32 is fitted to a position opposed to the light source 31 and below the sample stage 25.

It is to be noted that the sample holder 8 referred to above and employed in the practice of the present invention is not a sample holder going along with each sample S, but a sample holder that attached to the analyzing apparatus for placing the sample S thereon and can be replaced with another one in dependence on the size of the sample S to be analyzed. Also, the movement of the hole 81 in the pedestal of the sample holder, which is referred to hereinabove and hereinafter, means a movement of the hole 81 in the pedestal in, for example, an X-axis direction on the X-Y coordinate of the hole 81 in the pedestal when viewed from top.

Figure 3A:
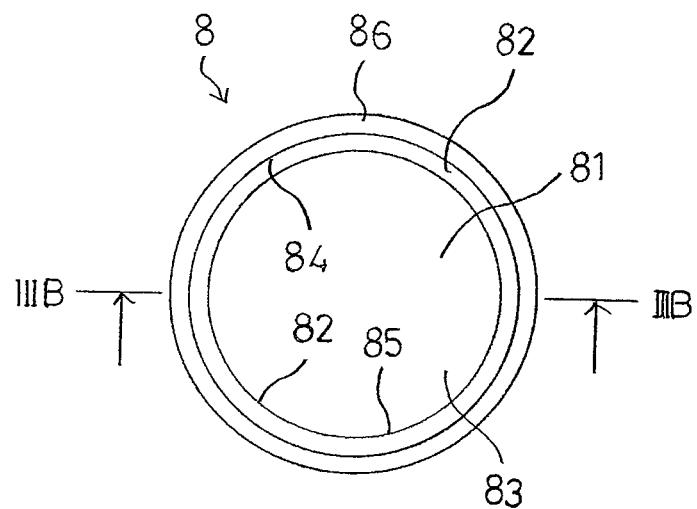
FIG. 3A is a schematic top plan view showing a sample holder for a sample of 200 mm in diameter, which is employable in the X-ray analyzing apparatus.
Figure 3B:
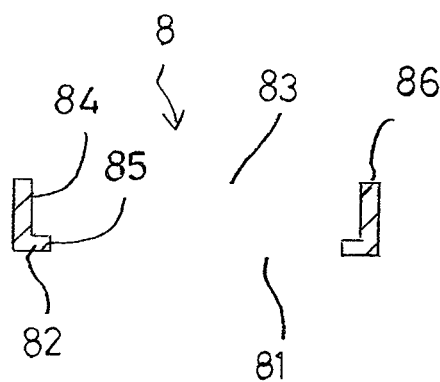
FIG. 3B is a cross sectional view taken along the line IIIB-IIIB in FIG. 3A.
Figure 4A:
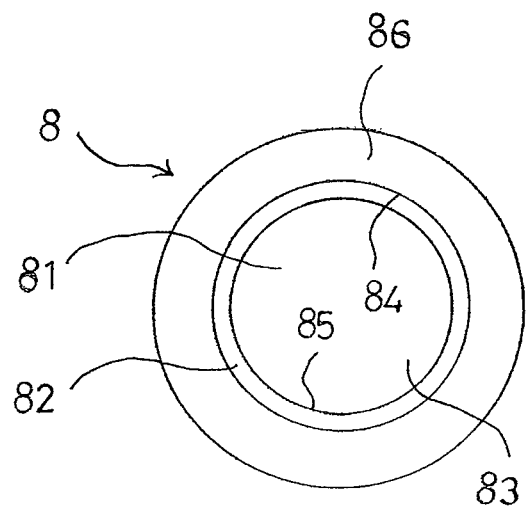
FIG. 4A is a schematic top plan view showing the sample holder for a sample of 150 mm in diameter, which is employable in the X-ray analyzing apparatus.
Figure 4B:
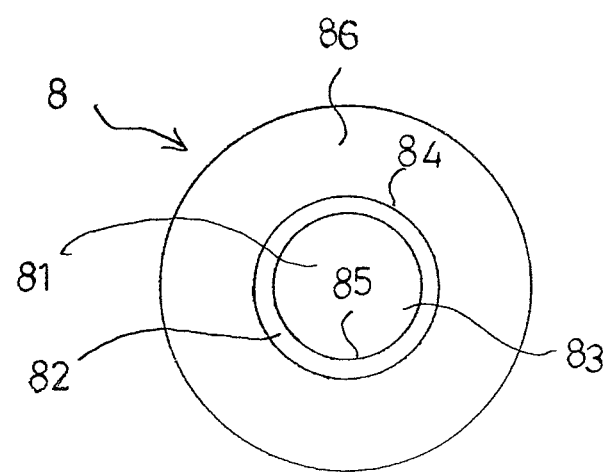
FIG. 4B is a schematic top plan view showing the sample holder for a sample of 100 mm in diameter, which is employable in the X-ray analyzing apparatus.

FIG. 3A schematically illustrates a top plan view of the sample holder 8 for the sample of 200 mm in diameter, and FIG. 3B illustrates a cross section thereof taken along the line IIIB-IIIB in FIG. 3A. As best shown in FIGS. 3A and 3B, the sample holder 8 has the insertion hole 83 for insertion therethrough of the sample S, a radially oriented end 84 of the insertion hole 83, the ring shaped pedestal 82 on which the sample S is placed, the hole 81 in the pedestal, the radially inward end 85 of the pedestal which is a radially oriented end of the hole, and an annular edge. FIG. 4A schematically illustrates a top plan view of the sample holder 8 for the sample of 150 mm in diameter and FIG. 4B schematically illustrates a top plan view of the sample holder 8 for the sample of 100 mm in diameter. Those sample holders 8 are made of the same material as that used for the sample holder for the sample of 200 mm in diameter, but have respective sample holder insertion holes 83 and pedestal holes 81, both having respective diameters differing from the diameters of the sample holder insertion hole 83 and pedestal hole 81 in the sample holder 8 for the sample of 200 mm in diameter.

As shown in FIG. 1, the analyzing chamber 105 includes an X-ray source 1 such as, for example, an X-ray tube for projecting primary X-rays 2 towards the sample S, and a detecting section 7 having a spectroscopic device (for example, LiF crystal) and a detector for spectroscopically analyzing secondary X-rays 4, emanating from the sample S when the latter is excited by the primary X-rays 2 from the X-ray source 1, and detecting the intensity of the secondary X-rays 4. During the analysis of the sample S, the sample stage 25 is moved by the shifting section 26 from the sample loading site 101 to the analyzing chamber 105 so that the sample S on the sample holder 8 can be exposed to the primary X-rays 2. The X-ray fluorescence spectrometer shown and described in connection with the preferred embodiment of the present invention is a wavelength dispersive X-ray fluorescence spectrometer of an upward irradiating and simultaneous multi-elements analyzing type and, hence, the detecting section 7 referred to above is a fixed type goniometer provided for each of elements to be measured.

The main body 100 further includes the sample holder identifying section 35 for moving the sample stage 25, on which the sample holder 8, to which the sample S is not transported by the transport section 23, is placed, from a reference position O, at which the transmissive type photo-sensor assembly 30 transmits the light presence signal, to a position, at which a light absence signal is transmitted, by means of the shifting section 26 in a direction radially of the hole 81 in the pedestal and for subsequently transmitting the sample holder identification signal identifying the type of the sample holder 8 in dependence on the distance L of movement from the reference position O; a determining section 40 for determining, based on the cassette identification signal, transmitted from the cassette identifying section 22, and the sample holder identifying signal, transmitted from the sample holder identifying section 35, whether or not the diameter of the sample to be accommodated within the cassette 21 and the diameter of the sample to be placed on the pedestal of the sample holder 8 match with each other; a display section 60 for displaying a structural diagram including the status of whether the sample holder replacement door 106 is opened or closed, the status of whether the lid 102 is opened or closed, the type of the cassette 21 identified by the cassette identifying section 22, the type of the sample holder 8 identified by the sample holder identifying section 35, the result determined by the determining section 40 and the status of operation of the apparatus; and a control section 50 for controlling the lid 102, the transport section 23 and the shifting section 26.

Figure 5A:
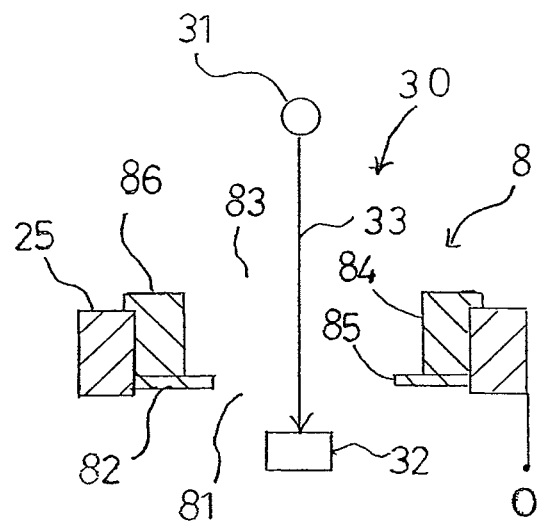
FIG. 5A is a diagram showing the sample holder held at a reference position in the X-ray analyzing apparatus.
Figure 5B:
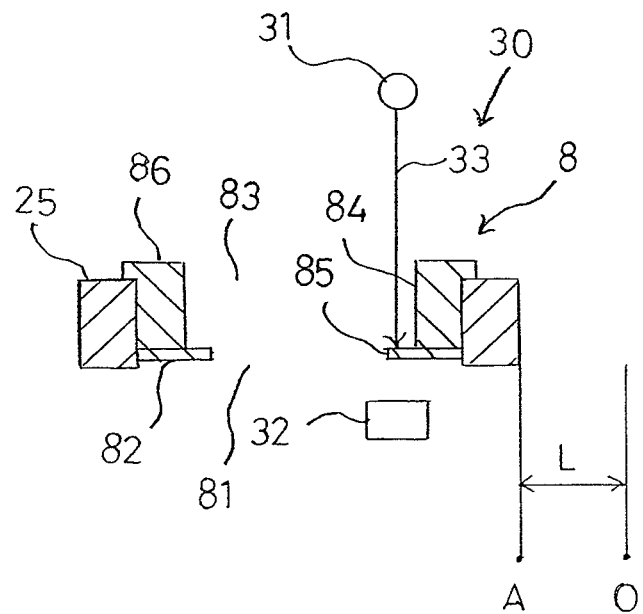
FIG. 5B is a diagram showing the sample holder held at a light shielding position in the X-ray analyzing apparatus.

As shown in FIG. 5A, by way of example, an end face position of the sample stage 25 in an initial condition on an analyzing chamber side is taken as the reference position O for the purpose of measurement of the moving distance L. The sample holder identifying section 35 generates the sample holder identifying signal for identifying the type of the sample holder 8 to the determining section 40 in dependence on the distance L of movement of the sample stage 25 from the reference position O to a light shielding position A, in the event that the sample stage 25 is moved from the reference position O in a direction radially of the hole 81 in the pedestal, for example, from a position, at which a light beam 33 emitted from a light source 31 passes through the center of the of the hole 81 in the pedestal as shown in FIG. 5A, to a position A at which the light beam 33 is shielded by the pedestal 82 as shown in FIG. 5B, and, hence, the light-sensitive detector 32 does no longer receive the light beam 33.

The sample holder identifying signal generated from the sample holder identifying section 35 is retained when the sample holder replacement door 106 is in a closed condition, but is invalidated when the sample holder replacement door 106 is released by the lock release switch 107 from a locked condition and is hence set in an opened condition.

Figure 6A:
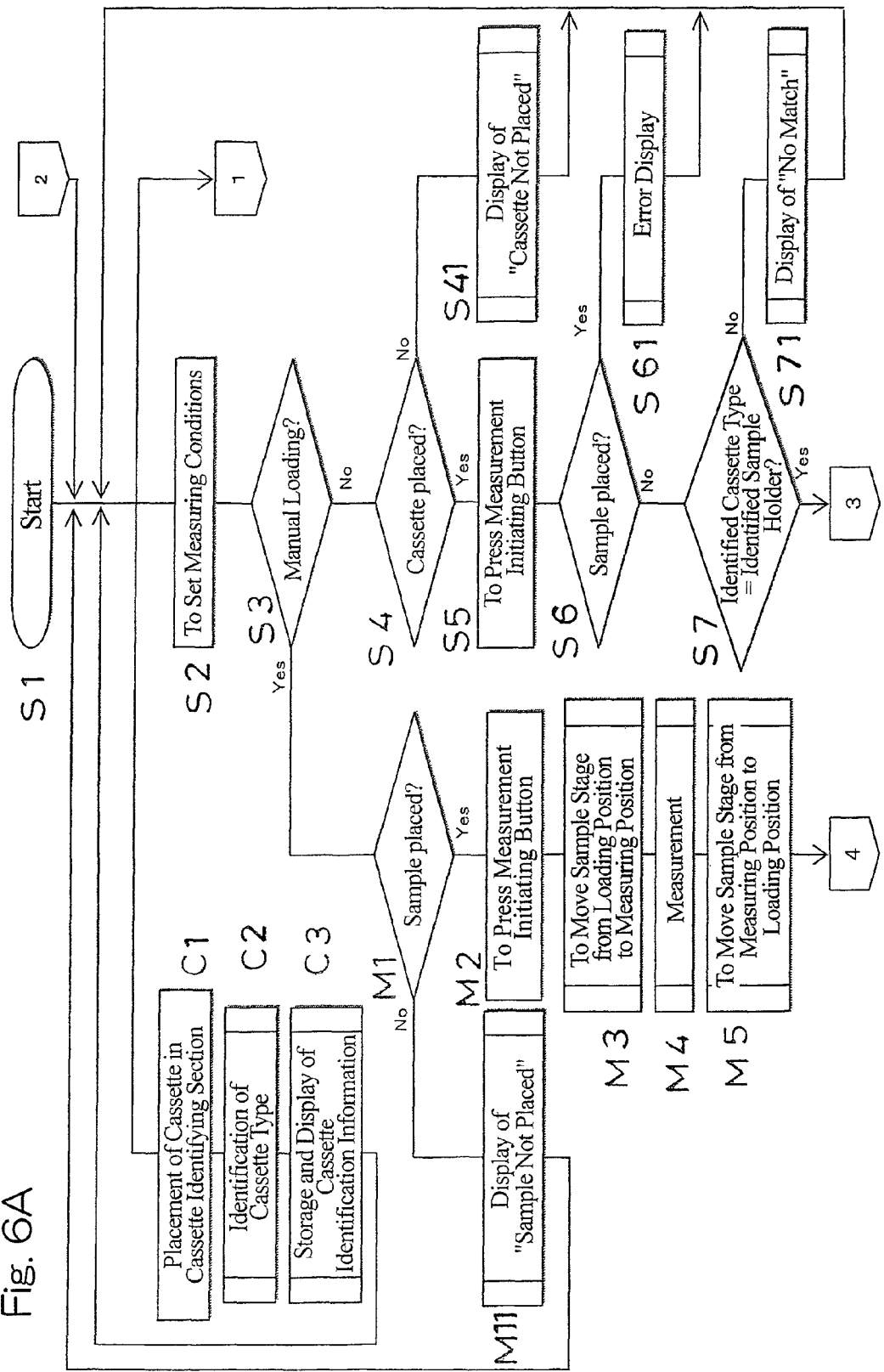
FIG. 6A is a diagram showing a first part of the entire flow of operation of the X-ray analyzing apparatus.
Figure 6B:
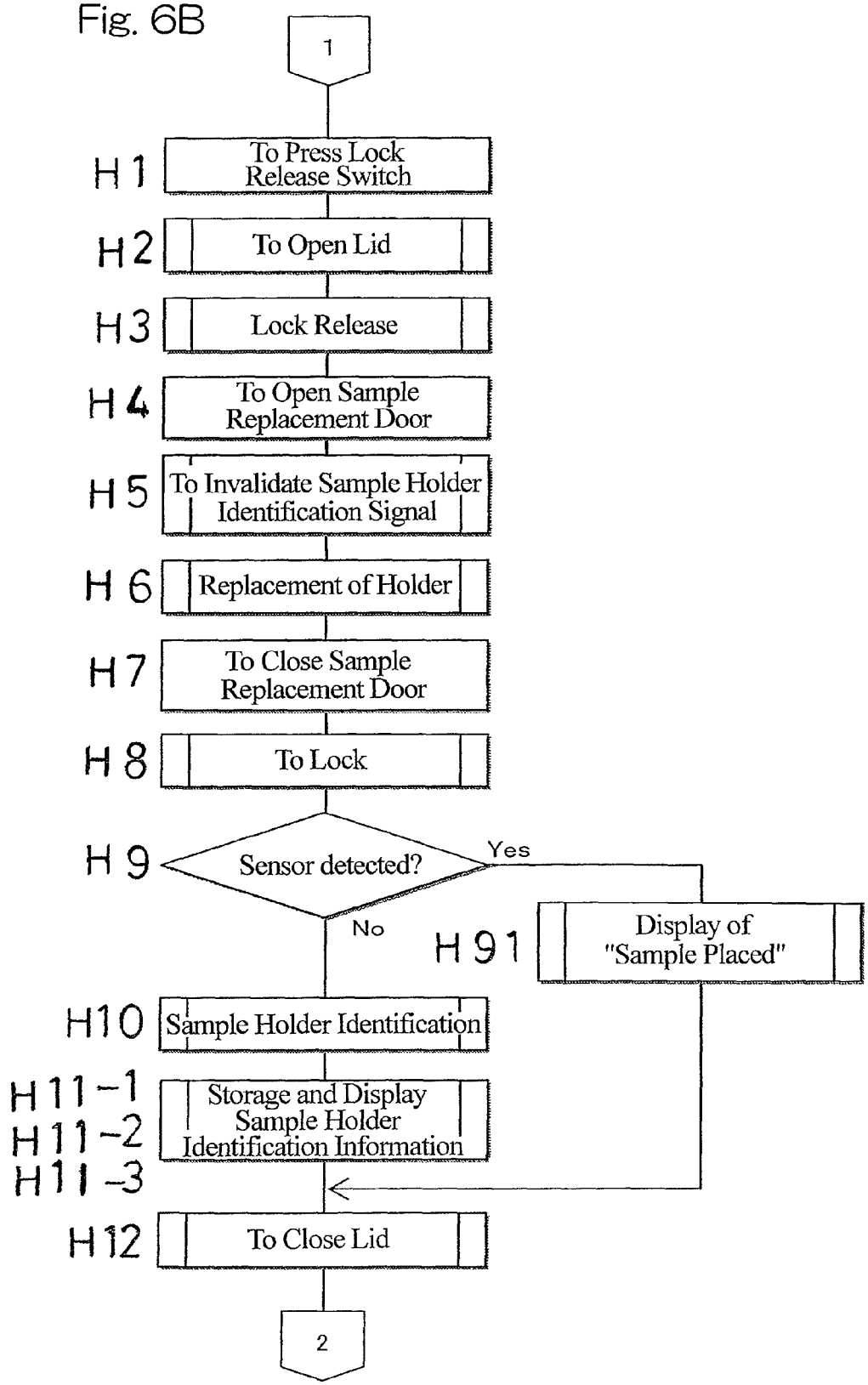
FIG. 6B is a diagram showing a second part of the entire flow of operation of the X-ray analyzing apparatus.
Figure 6C:
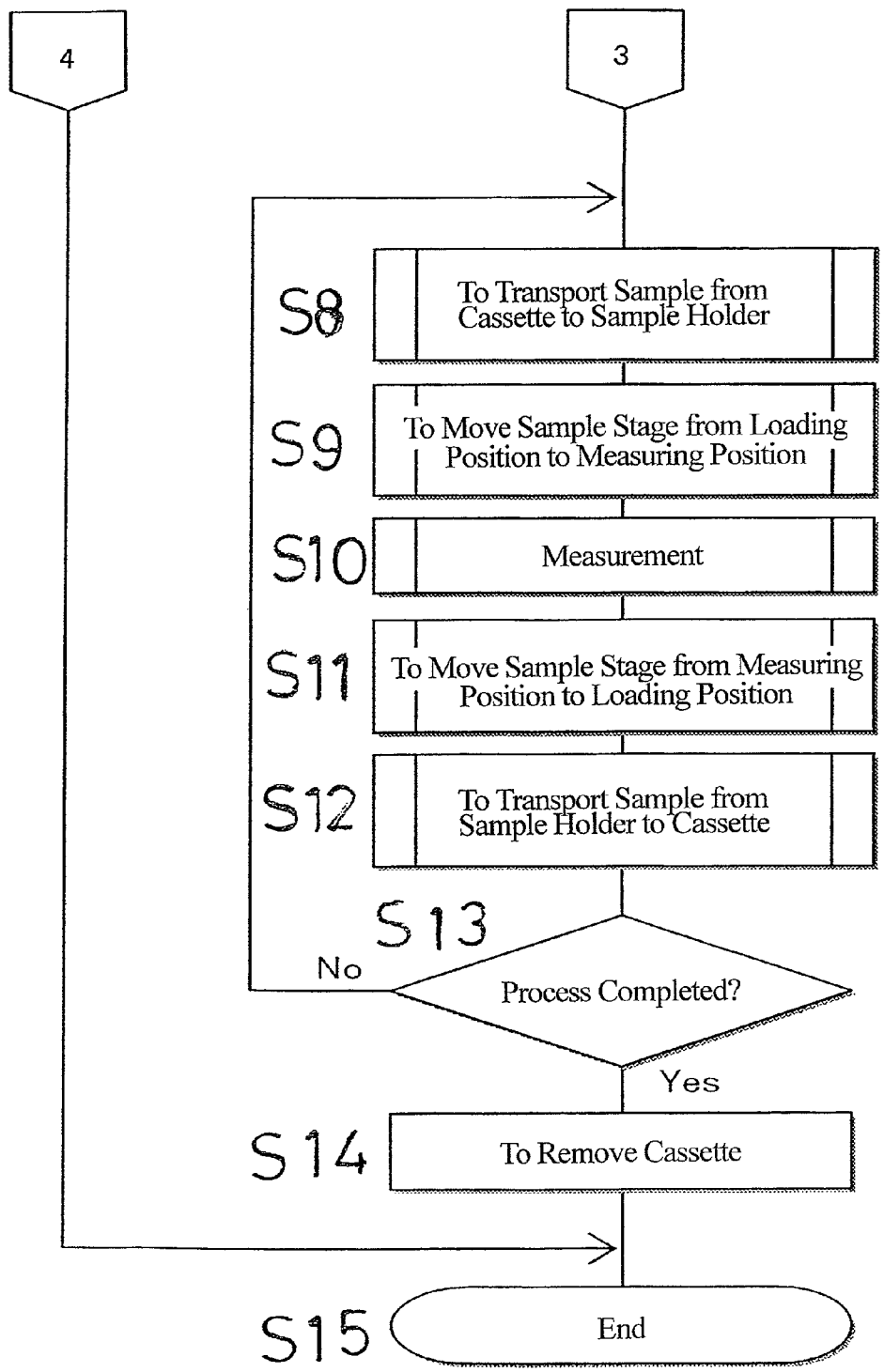
FIG. 6C is a diagram showing a third part of the entire flow of operation of the X-ray analyzing apparatus.
Figure 7:
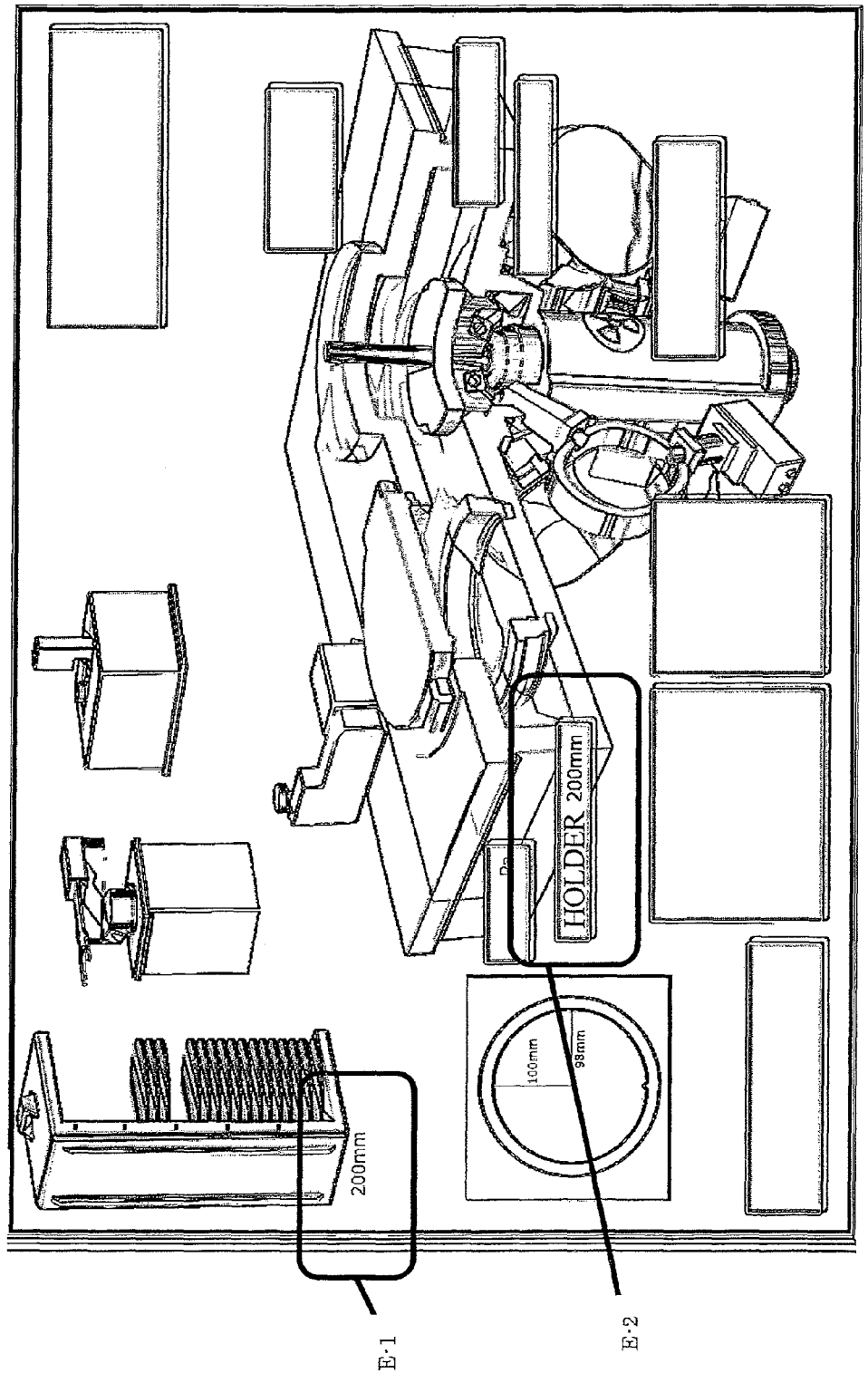
FIG. 7 is a schematic diagram showing the structure of the X-ray analyzing apparatus in a condition to identify the sample holder, being displayed in a display section employed in the X-ray analyzing apparatus.

Hereinafter, the operation of the X-ray analyzing apparatus according to the first embodiment of the present invention described hereinabove will be described with particular reference to FIGS. 6A, 6B and 6C showing the entire flow of operation of the apparatus. At step S1 shown in FIG. 6A, a main electric source switch of the apparatus is turned to initiate the operation. Then at step C1, an analyst puts a sample S in the form of, for example, a wafer of 200 mm in diameter in to a cassette 21 suited to the sample diameter and subsequently place such cassette 21 at the disposition site of the cassette identifying section 22. At step C2, the detector of the cassette identifying section 22, which is provided at a position appropriate to the type of the cassette 21, identifies the type of the cassette. At subsequent step C3, the cassette identifying section 22 generates a cassette identification signal, descriptive of the sample S of 200 mm in diameter, to the determining section 40 and then retains such identifying signal. Once the type of the cassette 21 has been identified, as shown in the structural diagram of the apparatus in FIG. 7 which is displayed by the display section 60, the legend "200 mm" is displayed in a rectangular block (E-1), drawn by a bold line at a top left portion of the screen, indicating that the type of the cassette 21 for the sample of 200 mm in diameter has been successfully identified.

Thereafter at step H1 shown in FIG. 6B, in an attempt to place the sample holder 8 for the sample of 200 mm in diameter on the sample stage 25 of the sample loading section 101, the analyst pushes the lock release switch 108 for the sample holder replacement door 106. At subsequent step H2, the lid 102 is controlled by the control section 50 to open upwardly. Then at step H3, the sample holder replacement door 106 is released from the locked condition to allow the sample holder replacement door 106 to be opened at any time. At step H4 following the step H3, the sample holder replacement door 106 is opened by the analyst, followed by step H5 at which the sample holder identification signal which has been retained is invalidated. Since as described above, when the sample holder replacement door 106 is closed, at which there is no likelihood of the sample holder 8 being replaced, the sample holder identification signal is retained as it stand, but the sample holder identification signal is invalidated only when the sample replacement door 106 is opened, at which the sample holder 8 is likely to be replaced, there is no necessity of identifying the sample holder 8 for each sample and the length of time required to accomplish the measurement can be reduced. Once the sample holder identification signal has been invalidated, placement of the wrong sample holder is avoided to ensure the operation by rendering the presence or absence of and the type of the sample holder 8 to remain unaccounted for and making it obligatory to conduct the identification of the sample holder again, Step H5 described above is followed by step H6, at which the analyst replaces the sample holder 8, which has been placed on the sample stage 25, with another sample holder 8 for the sample of 200 mm in diameter. At step H7, the analyst closes the sample holder replacement door 106. At step H8 after the closure of the sample holder replacement door 106 by the analyst, the control section 50 controls the locking mechanism 107 to lock the sample holder replacement door 106 in the closed condition. After the sample holder replacement door 106 has been locked in the closed condition, at step H9, the sample holder identifying section 35, upon receipt of the light presence signal from the transmissive type photo-sensor assembly 30, determined that the sample S is not placed on the sample holder 8.

Also, if the analyst erroneously places the sample holder on the sample stage 25 while the sample holder 8 holds the sample S therein, the sample holder identifying section 35 receives the light absence signal from the transmissive type photo-sensor assembly 30 at step H9, followed by step H91 at which that the sample S has been placed is displayed by the display section 60 and a stand-by state established with no identification of the sample holder 8 taking place.

When the sample holder identifying section 35 determines at step H9 that the sample S has not yet been placed in the sample holder 8, step H10 follows to enable the sample holder identifying section 35 to start identification of the sample holder 8 and the sample stage 25 is moved from the reference position O. In other words, when the sample holder identifying section 35 receives the light presence signal from the transmissive type photo-sensor assembly 30, the sample stage 25 is moved by the shifting section 26 from the reference position O in a direction radially of the hole 81 in the pedestal. In this way, since with the sample holder replacement door 106 held in the closed condition the type of the sample holder 8 is identified, it is possible to secure the safety during the operation brought about by, for example, the movement of the sample stage 25.

Figure 8:
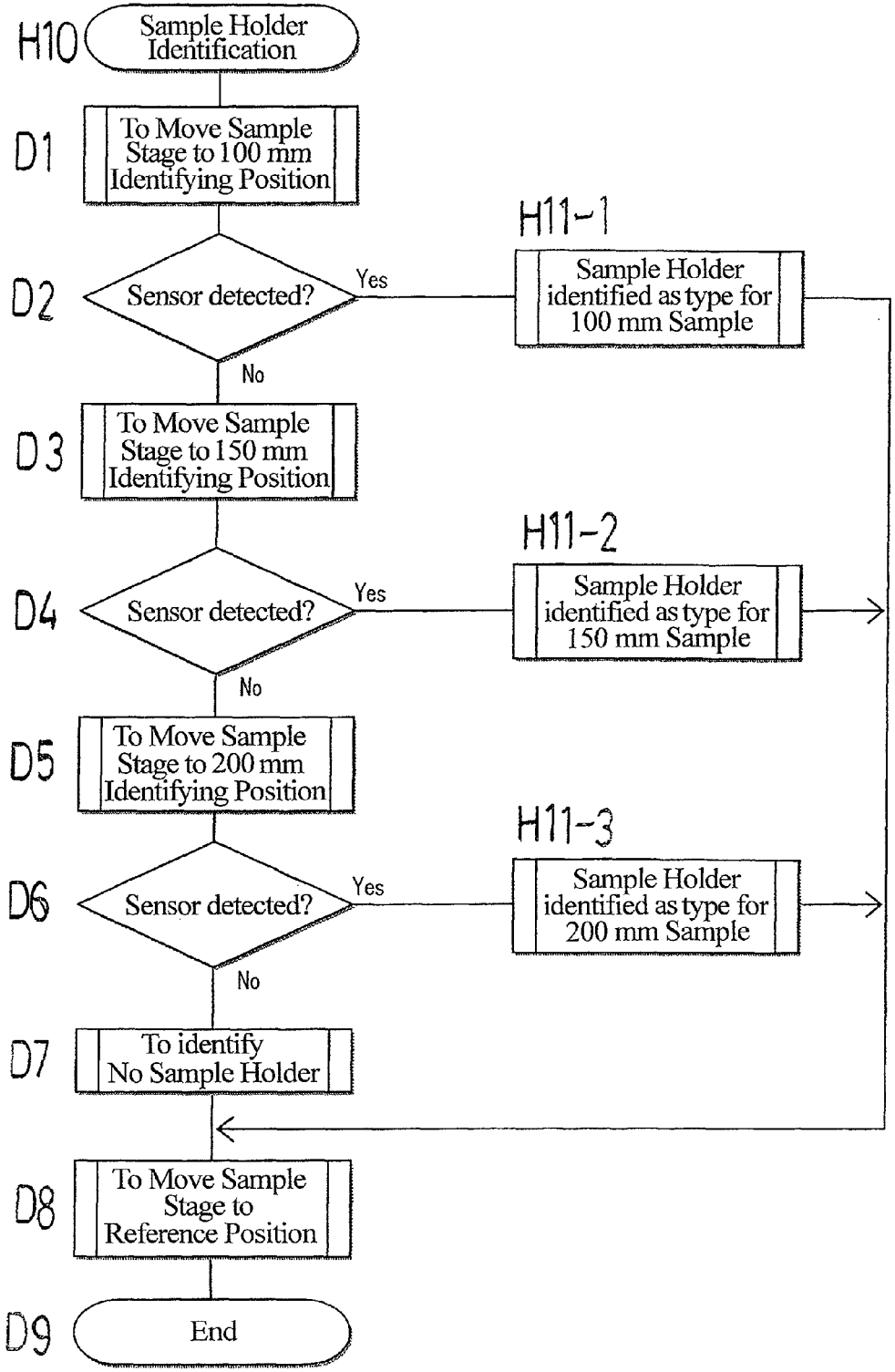
FIG. 8 is a flowchart showing the manner of identifying the sample holder employed in the X-ray analyzing apparatus.

Identification of the sample holder at steps H10 and H11 will now be described in detail with reference to the sample holder identifying flow shown in FIG. 8. At step D1 subsequent to the start of the sample holder identification, the sample stage 25 is moved a distance of 50 mm (i.e., to a 100 mm sample identifying position) from the reference position O by the shifting section 26 in a direction radially of the hole 81 in the pedestal. At subsequent step D2, the transmissive type photo-sensor assembly 30 detects whether or not the beam 33 from the light source 31 of the transmissive type photo-sensor assembly 30 is shielded by the pedestal 82 of the sample holder. When at the position to which the sample stage 25 has been moved the distance of 50 mm the beam 33 from the light source 31 of the transmissive type photo-sensor assembly 30 is shielded by the pedestal 82 of the sample holder and the light-sensitive detector 32 no longer receives the beam 33, the flow goes to step H11-1 at which the sample holder identifying section 35, upon receipt of the light absence signal from the transmissive type photo-sensor assembly 30, generates to the determining section 40 the sample holder identification signal indicative of the placement of the sample holder 8 for the sample of 100 mm in diameter and such identification signal is retained. In the event that decision at step D2 indicates that the beam 33 from the light source 31 is not shielded by the pedestal 82 of the sample holder, the flow goes to step D3 at which the movement of the sample stage 25 continues until the sample stage 25 moves the distance of 75 mm (i.e., to a 150 mm sample identifying position).

Then at step D4, the transmissive type photo-sensor assembly 30 detects whether or not the beam 33 from the light source 31 of the transmissive type photo-sensor assembly 30 is shielded by the pedestal 82 of the sample holder. When at the position to which the sample stage 25 has been moved the distance of 75 mm the beam 33 from the light source 31 of the transmissive type photo-sensor assembly 30 is shielded by the pedestal 82 of the sample holder, the flow goes to step H11-1 at which, in a manner similar to the sample holder 8 for the sample of 100 mm in diameter, the sample holder identifying section 35, upon receipt of the light absence signal from the transmissive type photo-sensor assembly 30, generates to the determining section 40 the sample holder identification signal indicative of the placement of the sample holder 8 for the sample of 150 mm in diameter and such identification signal is retained. In the event that decision at step D4 indicates that the beam 33 from the light source 31 is not shielded by the pedestal 82 of the sample holder, the flow goes to step D5 at which the movement of the sample stage 25 continues until the sample stage 25 moves the distance of 100 mm (i.e., to a 200 mm sample identifying position).

Then at step D6, the transmissive type photo-sensor assembly 30 detects whether or not the beam 33 from the light source 31 of the transmissive type photo-sensor assembly 30 is shielded by the pedestal 82 of the sample holder. When at the position to which the sample stage 25 has been moved the distance of 100 mm the beam 33 from the light source 31 of the transmissive type photo-sensor assembly 30 is shielded by the pedestal 82 of the sample holder, in a manner similar to the sample holder 8 for the sample of 100 mm in diameter, the sample holder identifying section 35, upon receipt of the light absence signal from the transmissive type photo-sensor assembly 30, generates to the determining section 40 the sample holder identification signal indicative of the placement of the sample holder 8 for the sample of 200 mm in diameter and such identification signal is retained. In the event that the sample holder 8 is identified at step H11-3, as shown in the structural diagram of the apparatus in FIG. 7, which is displayed on the display section 60, the legend "Holder 200 mm" is displayed in the rectangular block (E-2) drawn by the bold line at the bottom left portion of the screen, indicating that the sample holder 8 for the sample of 200 mm in diameter has been identified. In this way, the sample holder identifying section 35 identified the type of the sample holder 8 and the identification signal thereof transmits to the determining section 40 with the identification signal retained subsequently.

In the event that decision at step D6 indicates that at the position to which the sample stage 25 has been moved the distance of 100 mm, the beam 33 from the light source 31 has not been shielded by the pedestal 82 of the sample holder, the movement of the sample stage 25 is continued until the sample stage arrives at a limit position at which the sample stage 82 is stopped. If at this time the sample holder identifying section 35 receives the light presence signal generated by the transmissive type photo-sensor assembly 30, the flow goes to step D7 at which a signal indicating that the sample holder 8 has not been placed is transmitted to the determining section 40.

If at any of steps H11-1, H11-2 and H11-3 the sample holder has been identified, the flow goes to step D8 at which the sample stage 25 is moved to the reference position O by the shifting section 26. Then, if the operation to identify the sample holder 8, which takes place at any of steps H10, H11-1, H11-2 and H11-3, completes normally, the flow goes to step H12 shown in FIG. 6B and the lid 102 is closed accordingly.

Referring to FIG. 6A, at step S2, the analyst sets measuring conditions. At subsequent step S3, the analyst puts the sample S in to the sample holder 8 then placed on the sample stage 25 and the selects one of a manual loading mode (measurement by manual feed), in which measurement takes place after the sample stage 25 has been moved from a loading position (position at which the sample is placed) to a measuring position (position at which the sample is measured), and a mode other than the manual loading mode. If the manual loading mode is not selected, i.e., the mode other than manual loading mode is selected, the flow goes to step S4. If the manual loading mode is selected, the case will be described later.

At step S4 referred to above, decision is made to determine whether or not that the cassette 21 is placed by the cassette identifying section 22. If the cassette 21 is not placed, the flow goes to step S41 and the non-placement of the cassette 21 is displayed by the display section 60. If step S4 indicates that the cassette 21 has been placed, the flow goes to step S5 at which the analyst pushes a measurement initiating button (a start button) to initiate the measurement. At subsequent step S6, decision is made, in a manner similar to step H9 (shown in FIG. 6B), whether or not the sample has been placed. If the decision at step S6 indicates that the sample has been placed, the flow goes to step S61 at which a legend reading "Sample S found at Loading Port. Remove Sample at Loading Port" is displayed on the display section 60.

If the decision at step S6 indicates that the sample has not yet been placed, the flow goes to step S7 at which the determining section 40 determines, based on the cassette identification signal indicative of the diameter of the sample S, generated from the cassette identifying section 22, and the sample holder identifying signal, whether or not the diameter of the sample S to be accommodated in the cassette 21 and the diameter of the sample S to be placed on the pedestal of the sample holder 8 match with each other. As hereinbefore described, if the cassette 21 for 200 mm in diameter is arranged, based on the cassette identification signal from the cassette identifying section 22, which is indicative of the placement of the cassette 21 for 200 mm in diameter, and the sample holder identification signal indicative of the placement of the sample holder 8 for the sample of 200 mm in diameter, whether or not the cassette 21 for 200 mm in diameter and the sample holder 8 for 200 mm in diameter are matched with each other is determined. If the determining section 40 determines that they do not match with each other, the flow goes to step S71 at which a legend reading "Detected Sample Holder differs from Setting. Change Setting or Replace Sample Holder" is displayed on the display section 60.

If the decision at step S7 indicates the match, the flow goes to step S8 shown in FIG. 6C, at which the lid 102 is opened and the sample 8 is transported from the cassette 21 by the transport section 23 for placement in the sample holder 8. Then at step S9, the control section 50 causes the shifting section 26 to move the sample stage 25 to the measuring position within the analyzing chamber 105. At subsequent step S10, measurement of the sample S in accordance with the measuring conditions is initiated.

Thereafter, at step S11, the sample stage 25 is moved by the shifting section 26 from the measuring position within the analyzing chamber 105 to the loading position. At step S12, the sample S is transported by the transport section 23 from the sample holder 8 to the cassette 21. Then at step S13, decision is made to determine whether or not the process has to be terminated by the control section 50. In the event that another sample to be subsequently analyzed is available, the flow consisting of steps 8 to 13 is repeated. On the other hand, if the decision at step S13 indicates the absence of the sample to be subsequently analyzed, the flow goes to step S14 and the analyst removes the cassette 21 from the position at which it has been placed. Then, the measurement terminates at step S15.

With the X-ray analyzing apparatus designed according to the first embodiment of the present invention, since the sample holder 8 having no sample S placed therein is automatically identified by the transmissive type photo-sensor assembly 30 capable of detecting the presence or absence of the sample S, there is no need to use any indicium such as, for example, the sample identification label and/or the mask made of the specific element, and the sample holder 8 can be automatically identified before the sample S is transported to the sample holder 8.

It is to be noted that unless the diameter of the sample S to be accommodated within the cassette 21 and the diameter of the sample S to be placed on the pedestal of the sample holder 8 match with each other, the display section 60 upon receipt of a signal from the determining section 40 provides a visual indication that they do not match with each other, and the control section 50 retains the lid 102 in the closed condition and controls the transport section 23 so that the sample S will not be transported from the cassette 21 to the sample holder 8. In this way, the sample S will not be transported to the sample holder 8 unless the diameter of the sample S to be accommodated within the cassette 21 matches with the diameter of the sample S to be placed on the pedestal of the sample holder 8. Accordingly, the sample S, the diameter of which does not match with the diameter of the sample S to be accommodated within the sample holder 8, is not transported and, therefore, there is no possibility that the sample S and/or the apparatus will be contaminated and/or any trouble will be invited in the apparatus.

Although in the foregoing description, the light source 31 of the transmissive type photo-sensor assembly 30 has been shown and described as fitted above the lid 102 and the light-sensitive detector 32 has been shown and described as fitted at a position opposed to the light source 31 and below the sample stage 25 as shown in FIG. 1, the light-sensitive detector 32 may be fitted above the lid 102 and the light source 31 may be fitted at a position opposed to the light-sensitive detector 32 and below the sample stage 25 so that the type of the sample holder 8 can be identified by detecting the radially inward end 85 of the ring shaped pedestal of the sample holder 8.

As a modified form of the above described first embodiment of the present invention, the analyzing apparatus utilizing a reflective type photo-sensor assembly as the sample holder identifying section will now be described with particular reference to FIGS. 9A to 9C. It is, however, to be noted that since the analyzing apparatus utilizing the reflective type photo-sensor assembly differs from that utilizing the transmissive type photo-sensor assembly 30 shown in FIG. 1 in respect to the structure of the sample holder identifying section and the identifying operation performed thereby, only the details of the sample holder identifying section and the identifying operation thereof will be described.

Figure 9A:
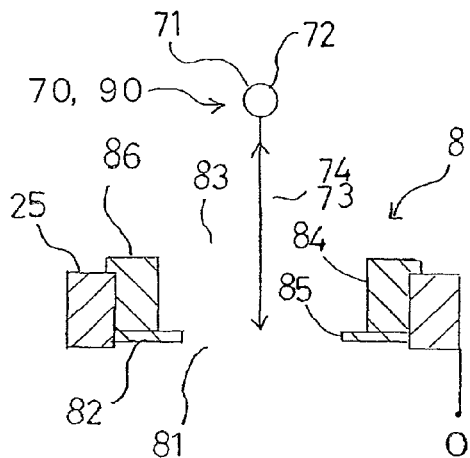
FIG. 9A is a diagram showing the sample holder held at the reference position in a modified form of the X-ray analyzing apparatus.
Figure 9B:
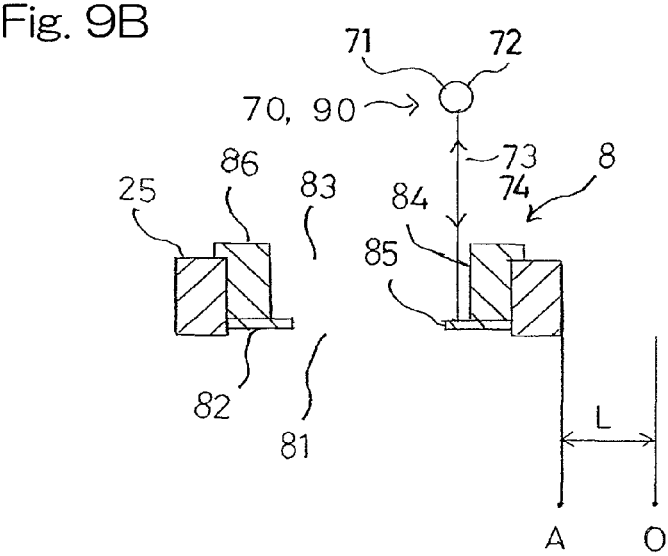
FIG. 9B is a diagram showing the sample holder employed in the modified form of the X-ray analyzing apparatus when a radially inward end of the pedestal is detected.
Figure 9C:
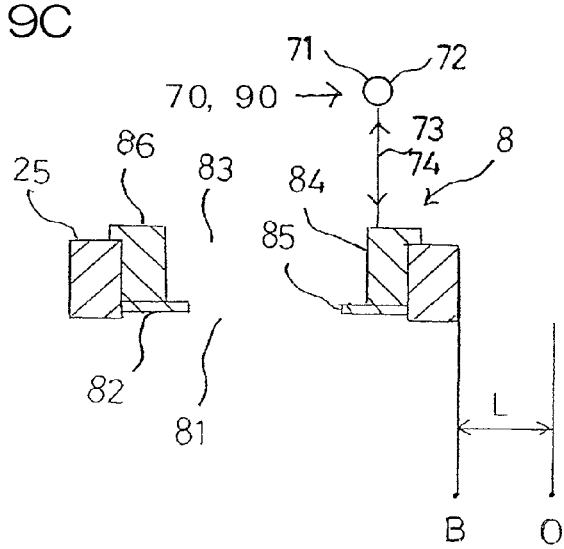
FIG. 9C is a diagram showing the sample holder employed in the modified form of the X-ray analyzing apparatus when a radially oriented end of an insertion hole is detected.

Referring first to FIG. 9A, the reflective type photo-sensor assembly 70 now identified by 70 is employed in the form of, for example, a laser type displacement sensor assembly of a trigonometrical survey system and includes a semiconductor laser 71 and a position sensitive detector (PSD) 72. The laser displacement sensor assembly 70 is of a design in which a laser beam 73 is emitted from the semiconductor laser 71 towards an object to be measured and the laser beam 74, which has been reflected on and from the object, is focused on the position sensitive detector 72 to form a beam spot so that the amount of displacement to the object to be measured can be ascertained by detecting the position of the beam spot.

At the outset, the sample holder identifying section 35 including the laser displacement sensor assembly 70 fitted above the lid 102 for detecting the radially inward end 85 of the ring shaped pedestal 82 will now be described. As shown in FIG. 9A, as is the case with that shown in and described with particular reference to FIG. 5A, the end position of the sample stage 25 on the side of the analyzing chamber, which is in the initial condition, is referred to as the reference position O for the purpose of measurement of the moving distance L. As shown in FIG. 9B, the sample holder identifying section 35 moves the sample stage 25, on which the sample holder 8 to which the sample S has not yet been transported by the transport section 23 is placed, from the reference position O in a direction radially of the hole 81 of the pedestal, while the laser beam 71 is projected from the semiconductor laser 71, to a position A, at which the spot changes from the spot position on the position sensitive detector 72 at the reference position O, that is, a position at which the laser beam 73 is projected onto the radially inward end 85 of the ring shaped pedestal 82, and generates the sample holder identification signal for identifying the type of the sample holder 8 in accordance with the distance L of movement from the reference position O, with the identification signal retained subsequently.

Hereinafter, the sample holder identifying section 35 including the laser displacement sensor assembly 70 for detecting the radially oriented end 84 of the insertion hole 83 will now be described. As shown in FIG. 9C, the sample holder identifying section 35 moves the sample stage 25, on which the sample holder 8 to which the sample S has not yet been transported by the transport section 23 is placed, from the reference position O in a direction radially of the insertion hole 83, while the laser beam 71 is projected from the semiconductor laser 71, to a position A (FIG. 9B), at which the spot changes from the spot position on the position sensitive detector 72 at the reference position O, that is, a position at which the laser beam 73 is projected onto the radially inward end 85 of the ring shaped pedestal 82, and further to a position B, at which the spot changes from the spot position at the radially inward end 85 of the ring shaped pedestal 82, that is, a position at which the laser beam 73 is projected onto the radially oriented end 84 of the insertion hole 83, and generates the sample holder identification signal for identifying the type of the sample holder 8 in accordance with the distance L of movement from the reference position O, with the identification signal retained subsequently.

Although the sample holder identification with the laser type displacement sensor assembly that will take place at any of the steps H10, H11-1, H11-2 and H11-3 is different from that with the transmissive type photo-sensor assembly, the identifying stage proceeds in sequence of steps similar to those in the sample holder identifying flow.

By the sample holder identifying section 35 including the laser type displacement sensor assembly 70 and detecting which one of the radially inward end 85 of the ring shaped pedestal and the radially oriented end 84 of the insertion hole is detected, how the laser type displacement sensor assembly 70 detects whether or not the sample S is placed in the sample holder 8 will now be described. Referring to step H9 shown in FIG. 6B, when the sample stage 25 is held at the reference position O, and when the sample holder identifying section 35 receives a signal indicative of the spot position to which the spot position on the position sensitive detector 72 at the reference position O has changed, the placement of the sample S in the sample holder 8 is determined and a sample presence signal indicative of the sample S having been placed is then generated, followed by step H91 at which the placement of the sample S in the sample holder 8 is visually indicated by the display section 60. At step S6 shown in FIG. 6A, determination of whether or not the sample is placed is carried out in a manner similar to that at step H9 shown in FIG. 6B. If the sample is placed, the flow goes to step S61 at which an error warning reading "Sample S found at Loading Port. Remove Sample at Loading Port" is displayed on the display section 60. At step M1 shown in FIG. 6A, determination of whether or not the sample has been placed is carried out in a manner similar to that at step H9 shown in FIG. 6B. If the sample is not placed, the flow goes to step M11 at which a legend representative of the sample not placed is displayed on the display section 60.

The analyzing apparatus utilizing an electric capacitance sensor assembly as the sample holder identifying section according to a further modified form of the first embodiment of the present invention will be described hereinafter. It is, however, to be noted that since the analyzing apparatus utilizing the electric capacitance sensor assembly differs from that utilizing the transmissive type photo-sensor assembly 30 shown in FIG. 1 in respect to the structure of the sample holder identifying section and the identifying operation performed thereby, only the details of the sample holder identifying section and the identifying operation thereof will be described.

The electric capacitance sensor assembly operates on the detecting principle that the electric capacitance formed between an electrode of an oscillating circuit, built in the sensor assembly, and an object to be measured changes with distance between such electrode and such object.

The device in which the sample holder identifying section 35 including the electric capacitance sensor assembly, now identified by 90, for detecting the radially inward end 85 of the pedestal will be first described. As shown in FIG. 9A, in a manner similar to that shown in and described with reference to FIG. 5A, the end face position of the sample stage 25 in the initial condition on the analyzing chamber side is taken as the reference position O for the purpose of measurement of the moving distance L. As shown in FIG. 9B, the sample holder identifying section 35 generates the sample holder identifying signal for identifying the type of the sample holder 8 to the determining section 40 in dependence on the distance L of movement from the reference position O, in the event that the sample stage 25, on which the sample holder 8 to which the sample S has not yet been transported by the transport section 23 is placed, is moved from the reference position O in a direction radially of the hole 81 in the pedestal to a position A, at which the detected electric capacitance of the electric capacitance sensor assembly 90 increases from the electric capacitance at the reference position O, that is, until the electric capacitance sensor assembly 90 is brought to a position immediately above the radially inward end 85 of the ring shaped pedestal 82, and then retain such identifying signal.

The sample holder identifying section 35 including the electric capacitance sensor assembly 90 for detecting the radially oriented end 84 of the insertion hole 83, will now be described. As shown in FIG. 9C, the sample holder identifying section 35 generates the sample holder identifying signal for identifying the type of the sample holder 8 to the determining section 40 in dependence on the distance L of movement from the reference position O, in the event that the sample stage 25, on which the sample holder 8 to which the sample S has not yet been transported by the transport section 23 is placed, is moved from the reference position O in a direction radially of the insertion hole 83 to a position A (shown in FIG. 9B), at which the detected electric capacitance of the electric capacitance sensor assembly 90 increases from the electric capacitance at the reference position O, that is, until the electric capacitance sensor assembly 90 is brought to a position immediately above the radially inward end 85 of the ring shaped pedestal 82, and further to a position B, at which the detected electric capacitance of the electric capacitance sensor assembly 90 increases from the electric capacitance at the radially inward end 85 of the ring shaped pedestal 82, that is, until the electric capacitance sensor assembly 90 is brought to a position immediately above the radially oriented end 84 of the insertion hole 83, and then the sample holder identifying section 35 retains such identifying signal.

Although the sample holder identification with the electric capacitance sensor assembly that will take place at any of the steps H10, H11-1, H11-2 and H11-3 is different from that with the transmissive type photo-sensor assembly, the identifying stage proceeds in sequence of steps similar to those in the sample holder identifying flow.

By the sample holder identifying section 35 including the electric capacitance sensor assembly 90 and detecting either one of the radially inward end 85 of the ring shaped pedestal or the radially oriented end 84 of the insertion hole, how the electric capacitance sensor assembly 90 detects whether or not the sample S is placed in the sample holder 8 will now be described. At step H9 shown in FIG. 6B, when the sample stage 25 is held at the reference position O, and when the electric capacitance sensor assembly 90 receives a signal indicative of the electric capacitance which has changed from the electric capacitance at the reference position O, the sample holder identifying section 35 determines that the sample S has been placed in the sample holder 8 and then generates the sample presence signal, followed by step H91. At step H91, the display section 60 displays a legend descriptive of the sample S having been placed. At step S6 shown in FIG. 6A, determination is made to determine, in a manner similar to that at step H9 shown in FIG. 6B, whether or not the sample is placed. If the sample has been placed, the flow goes to step S61, and the display section 60 displays an error message reading "Sample S found at Loading Port. Remove Sample at Loading Port". At step M1 shown in FIG. 6A, determination is made to determine, in a manner similar to that at step H9 shown in FIG. 6B, whether the sample has been placed. If no sample has yet been placed, the flow goes to step M11 at which the display section 60 displays the legend that the sample has not yet been placed.

Since even with the reflective type photo-sensor assembly (the laser type displacement sensor) or the electric capacitance sensor assembly, the sample holder S can be automatically identified in a manner similar to that with the transmissive type photo-sensor assembly, functions and effects similar to those afforded by the transmissive type photo-sensor assembly can be exhibited.

The apparatus according to the previously described first embodiment of the present invention is the X-ray fluorescence spectrometer and, in order to avoid a possible contamination of the sample or the sample holder, the sensor for detecting the sample or the sample holder is preferably employed in the form of a non-contact type sensor that does not contact the sample or the sample holder directly, for example, a transmissive type photo-sensor, a reflective type photo-sensor (a laser type displacement sensor) or an electric capacitance sensor.

Hereinafter, the analyzing apparatus according to a second preferred embodiment of the present invention will be described. While the apparatus according to the previously described first embodiment of the present invention best shown in FIG. 1 is the X-ray fluorescence spectrometer of an upward irradiating type, including the sample holder having the hole 81 best shown in FIGS. 3A and 3B and the sample holder identifying section utilizing one of the transmissive type photo-sensor assembly, the reflective type photo-sensor assembly (the laser type displacement sensor) and the electric capacitance sensor assembly, the analyzing apparatus according to the second embodiment of the present invention is an X-ray fluorescence spectrometer of a downward irradiating type, including a sample holder having no hole 81, and a sample holder identifying section utilizing the reflective type photo-sensor assembly (the laser type displacement sensor) or the electric capacitance sensor assembly and only the difference between it and the analyzing apparatus of the previously described first embodiment will be described.

Figure 10:
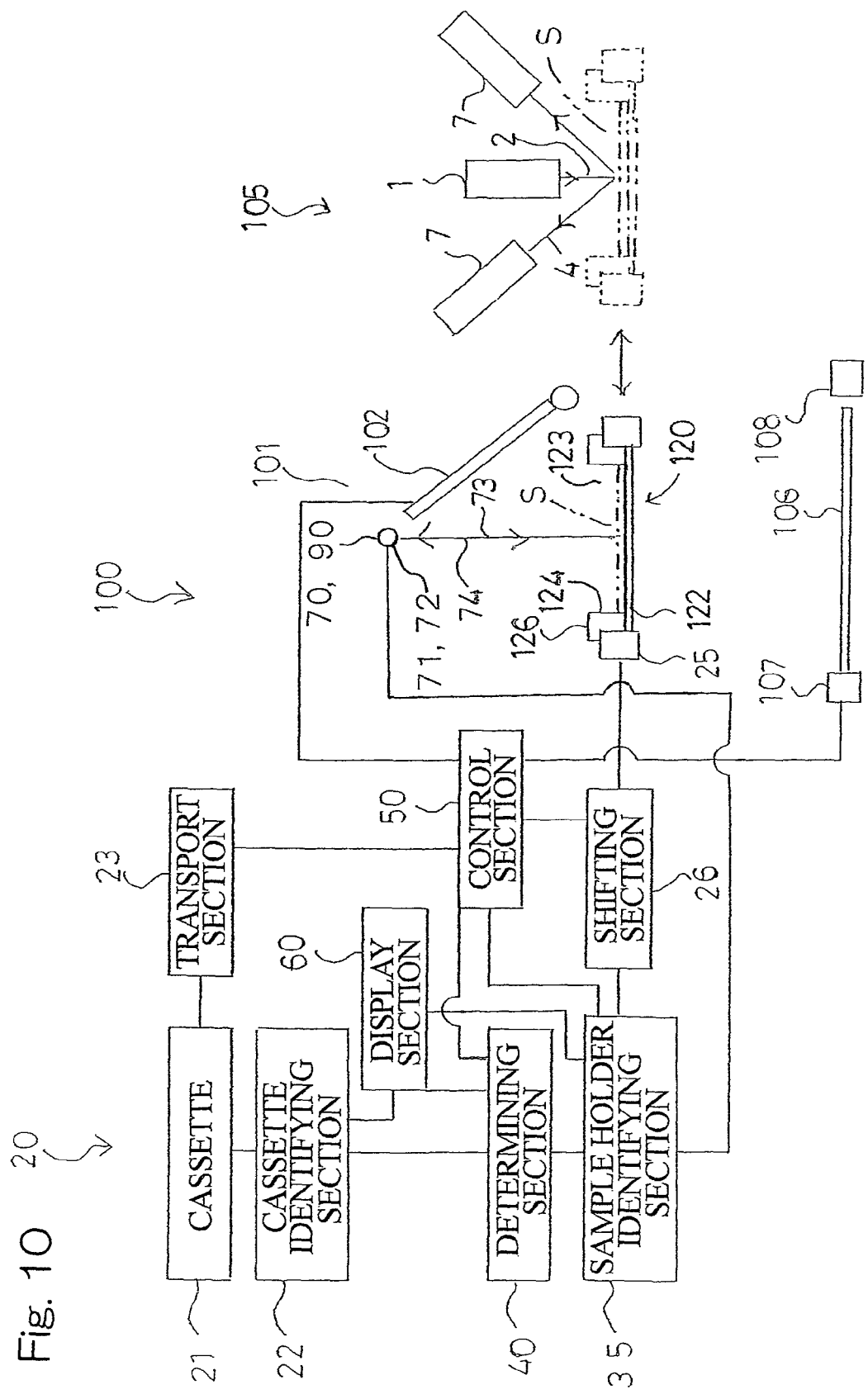
FIG. 10 is a schematic diagram showing the X-ray analyzing apparatus according to a second preferred embodiment of the present invention.

Referring now to FIG. 10, the analyzing apparatus according to the second preferred embodiment of the present invention is a wavelength dispersive X-ray fluorescence spectrometer of a downward irradiating and simultaneous multi-elements analyzing type, and then the detecting section 7 is a fixed type goniometer provided for each of the elements to be measured. The analyzing chamber 105 includes an X-ray source 1 such as, for example, an X-ray tube for projecting primary X-rays 2 towards the sample S, and a detecting section 7 having a spectroscopic device (for example, LiF crystal) and a detector for spectroscopically analyzing secondary X-rays 4, emanating from the sample S when the latter is excited by the primary X-rays 2 from the X-ray source 1, and detecting the intensity of the secondary X-rays 4.

The analyzing apparatus in which the sample holder identifying section 35 makes use of the laser type displacement sensor assembly 70 for detecting a radially oriented end 124 of an insertion hole 123 will now be described. As best shown in FIG. 10, the main body 100 includes a sample holder 120 (best shown in FIGS. 11A and 11B), which has an insertion hole 123, of a diameter corresponding to the diameter of the sample S and through which the sample S is inserted from above, and a disc shaped pedestal 122 for supporting thereon the sample S, and a sample holder identifying section 35 for detecting the radially oriented end 124 of the insertion hole 123 and generating the sample holder identification signal for identifying the type of a sample holder 120 corresponding to the diameter of the sample S to be placed.

Figure 11A:
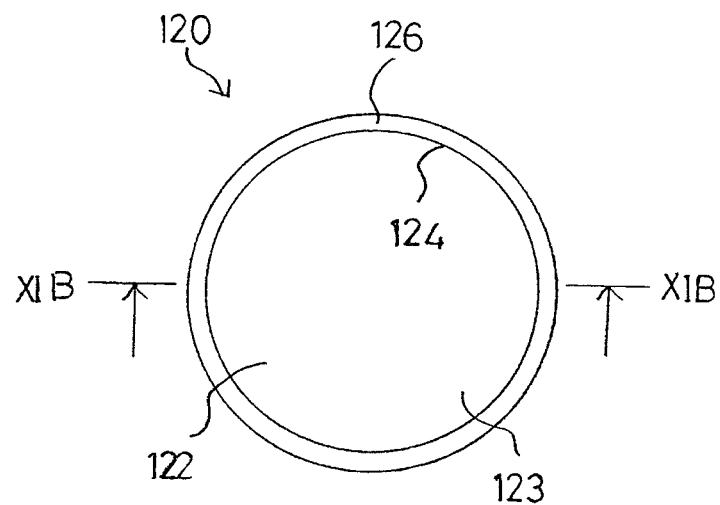
FIG. 11A is a schematic top plan view showing the sample holder for a sample of 200 mm in diameter employable in the X-ray analyzing apparatus shown in FIG. 10.
Figure 11B:
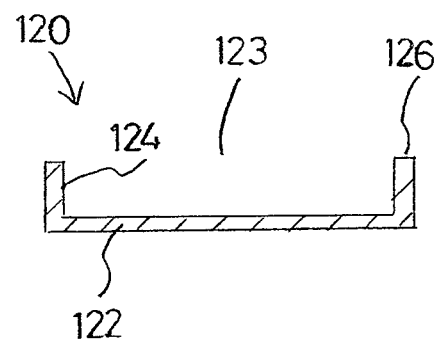
FIG. 11B is a cross sectional view taken along the line XIB-XIB in FIG. 11A.

FIG. 11A is a schematic top plan view of the sample holder 120 for the sample of 200 mm in diameter and FIG. 11B is a cross section taken along the line XIB-XIB in FIG. 11A. As shown in FIGS. 11A and 11B, the sample holder 120 has the insertion hole 123 through which the sample S is inserted; the radially oriented end 124 of the insertion hole 123; the disc shaped pedestal 122 on which the sample S is placed; and an annular edge 126. In the sample holders 120 for the samples of 200 mm, 150 mm, and 100 mm in diameter, respectively, outer diameters of the annular edges 126 of those sample holders remain the same, but the insertion holes 123 in those sample holders have varying diameters that correspond respectively to the diameters of the samples, noting that the same material is used to form those sample holders.

Figure 12A:
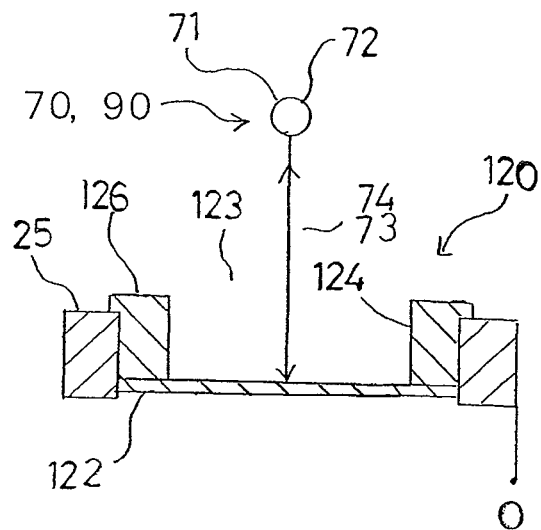
FIG. 12A is a schematic diagram showing the sample holder held at the reference position in the X-ray analyzing apparatus shown in FIG. 10.
Figure 12B:
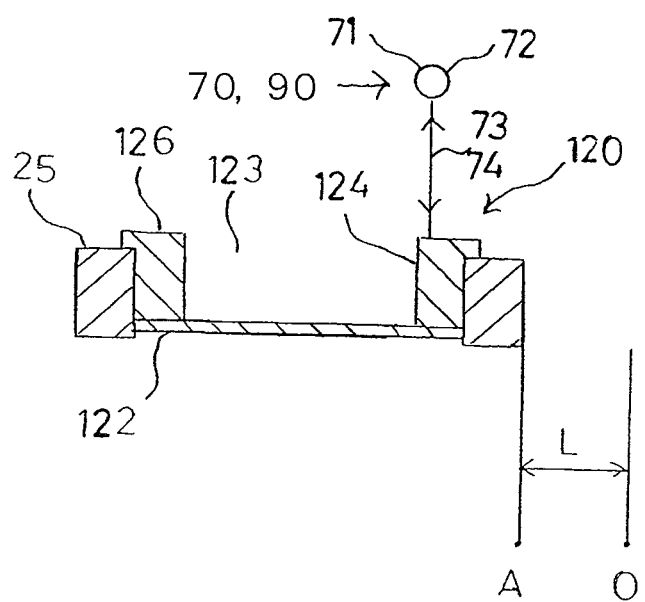
FIG. 12B is a schematic diagram showing the sample holder employed in the X-ray analyzing apparatus shown in FIG. 10 when the radially oriented end of the insertion hole is detected.

As shown in FIG. 12A, the sample holder identifying section 35 moves the sample stage 25, having placed thereon the sample holder 120 to which the sample S is not transported by the transport section 23, from the reference position O in a direction radially of the insertion hole 123 while the laser beam 73 from the semiconductor laser 71 is radiated. Subsequently, as shown in FIG. 12B, the sample stage 25 is moved to the position A at which the spot changes from the spot position on the position sensitive detector 72 at the reference position O, that is, the position at which the laser beam 73 projects onto the radially oriented end 124 of the insertion hole 123, and generates to the determining section 40, the sample holder identification signal for identifying the type of the sample holder 120, in dependence on the distance L of movement from the reference position O, with the identification signal retained subsequently.

By the sample holder identifying section 35 including the laser type displacement sensor assembly 70 and detecting the radially oriented end 124 of the insertion hole, the manner of how detection is made as to whether or not the sample S is placed in the sample holder 8 will now be described. As shown in FIG. 12A, while the sample stage 25 is held at the reference position O, the sample holder identifying section 35, upon receipt of a signal indicative of the spot position which have changed from the spot position on the position sensitive detector 72 at the reference position O, determines that the sample S has been placed in the sample holder 8 and then generates the sample presence signal indicative of the placement of the sample S in the sample holder 8, with such sample presence signal retained subsequently.

Hereinafter, the analyzing apparatus according to a modified form of the second embodiment of the present invention, in which the electric capacitance sensor assembly 90 is employed as the sample holder identifying section, will be described. Since the analyzing apparatus according to this modified form of the second embodiment differs from the X-ray fluorescence spectrometer shown in and described with particular reference to FIG. 10 in respect of the structure of the sample holder identifying section 35 and the identifying operation, only the structure of the sample holder identifying section 35 and the identifying operation will be described.

The sample holder identifying section 35 including the electric capacitance sensor assembly 90 for detecting the radially oriented end 124 of the insertion hole 123 will be described. As shown in FIG. 12A, the sample holder identifying section 35 moves the sample stage 25 having placed thereon the sample holder 120 to which the sample S is not transported, from the reference position O in a direction radially of the insertion hole 123, as shown in FIG. 12B, to the potion A at which the electric capacitance detected by the electric capacitance sensor assembly 90 increases from the electric capacitance at the reference position O, that is, until the electric capacitance sensor 90 is brought to a position immediately above the radially oriented end 124 of the insertion hole 123, and then generates to the determining section 40 the sample holder identification signal for identifying the type of the sample holder 120 in dependence on the distance L of movement from the reference position O, with such identification signal retained subsequently.

By the sample holder identifying section 35 including the electric capacitance sensor assembly 90 and detecting the radially oriented end 124 of the insertion hole, the manner of how detection is made as to whether or not the sample S is placed in the sample holder 120 will now be described. As shown in FIG. 12A, while the sample stage 25 is held at the reference position O, the electric capacitance sensor assembly 90, upon receipt of a signal indicative of the electric capacitance, which has changed from the electric capacitance at the reference position O, determines that the sample S has been placed in the sample holder 8 and then generates the sample presence signal indicative of the placement of the sample S in the sample holder 120, with such sample presence signal retained subsequently.

Since the apparatus according to the second embodiment is capable of automatically identifying the sample holder 8 in a manner similar to that performed by the apparatus according to the previously described first embodiment, functions and effects similar to those afforded by the apparatus according to the previously described first embodiment can be obtained.

The X-ray fluorescence spectrometer according to a third preferred embodiment of the present invention will be described in detail hereinafter. The analyzing apparatus according to the third embodiment is an X-ray fluorescence spectrometer of the downward irradiating type as is the case with the analyzing apparatus according to the second embodiment, which includes a sample holder, having an insertion hole of a diameter corresponding to the diameter of the sample and into which the sample is inserted from above, and a disc shaped pedestal for supporting the sample thereon, and also having a recessed inlet of a round configuration defined in the disc shaped pedestal and which also includes the sample holder identifying section having the reflective type photo-sensor assembly (the laser type displacement sensor) or the electric capacitance sensor assembly, and, since those structures and the operation thereof are different from those in the previously described second embodiment, only the different in structure and operation will be described.

The sample holder identifying section 35 including the laser type displacement sensor 70 for detecting a radially oriented end 135 of the round recessed inlet 131 in a disc shaped pedestal 132 of the sample holder 130 will be described.

Figure 13A:
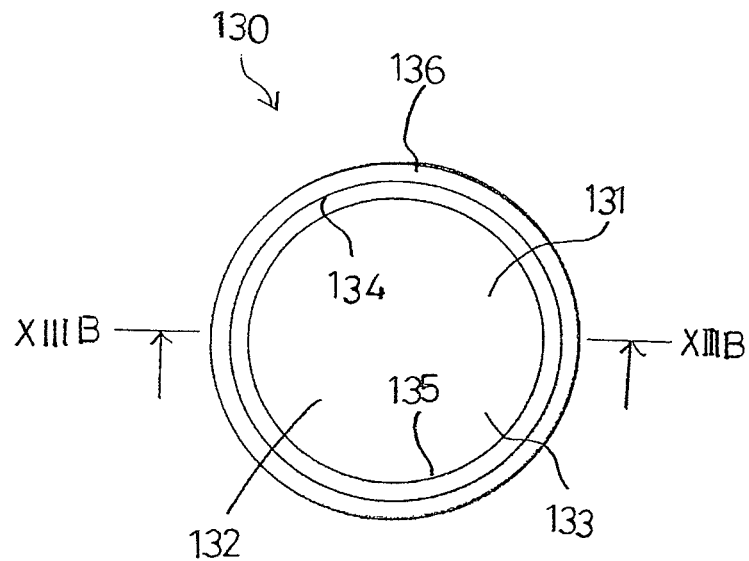
FIG. 13A is a schematic top plan view showing the sample holder for a sample of 200 mm in diameter employable in the X-ray analyzing apparatus according to a third preferred embodiment of the present invention.
Figure 13B:
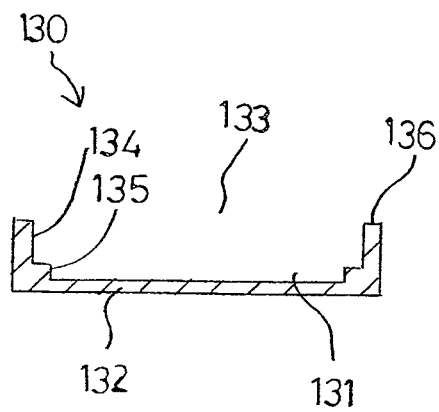
FIG. 13B is a cross sectional view taken along the line XIIIB-XIIIB in FIG. 13A.

FIG. 13A is a schematic top plan view of the sample holder 130 for the sample of 200 mm in diameter and FIG. 13B is a cross sectional view taken along the line XIIIB-XIIIB in FIG. 13A. As shown in FIGS. 13A and 13B, the sample holder 130 has an insertion hole 133 through which the sample S is inserted, a radially oriented end 134 of the insertion hole 133, and a disc shaped pedestal 132 for supporting the sample S thereon, and the disc shaped pedestal 132 has a recessed inlet 131 of a round configuration, a radially oriented end 135 of the recessed inlet 131, and an annular edge 136. In the sample holders 130 for the samples of 200 mm, 150 mm, and 100 mm in diameter, respectively, outer diameters of the annular edges 136 of those sample holders remain the same, but the insertion holes 133 and the recessed inlets 131 in those sample holders have varying diameters that correspond respectively to the diameters of the samples, noting that the same material is used to form those sample holders.

Figure 14A:
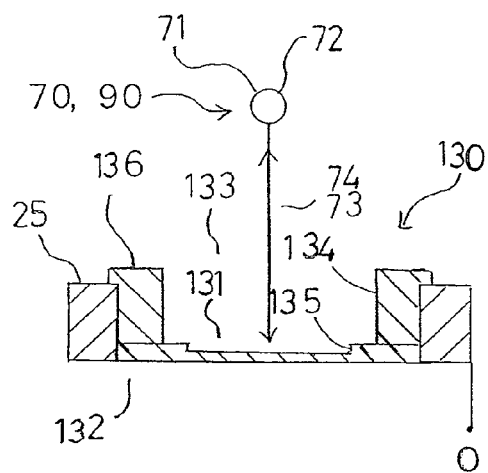
FIG. 14A is a schematic diagram showing the sample holder held at the reference position in the X-ray analyzing apparatus shown in FIG. 13A.
Figure 14B:
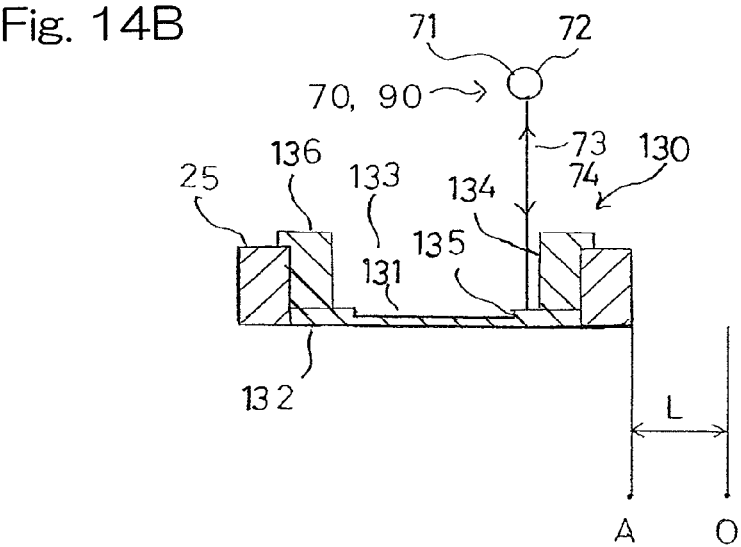
FIG. 14B is a schematic diagram showing the sample holder employed in the X-ray analyzing apparatus shown in FIG. 13A when a radially oriented end of a recessed inlet defined in a disc shaped pedestal is detected.

As shown in FIG. 14A, the sample holder identifying section 35 moves the sample stage 25, having placed thereon the sample holder 120 to which the sample S is not transported by the transport section 23, from the reference position O in a direction radially of the recessed inlet 131 while the laser beam 73 from the semiconductor laser 71 is radiated. Subsequently, as shown in FIG. 14B, the sample stage 25 is moved to the position A at which the spot changes from the spot position on the position sensitive detector 72 at the reference position O, that is, the position at which the laser beam 73 projects onto the radially oriented end 135 of the recessed inlet, and generates to the determining section 40, the sample holder identification signal for identifying the type of the sample holder 130, in dependence on the distance L of movement from the reference position O, with the identification signal retained subsequently.

The sample holder identifying section 35 including the laser type displacement sensor assembly 70 for detecting the radially oriented end 134 of the insertion hole 133 in the sample holder 130 including the disc shaped pedestal 132 having defined therein the recessed inlet 131 of the round configuration, will now be described.

Figure 14C:
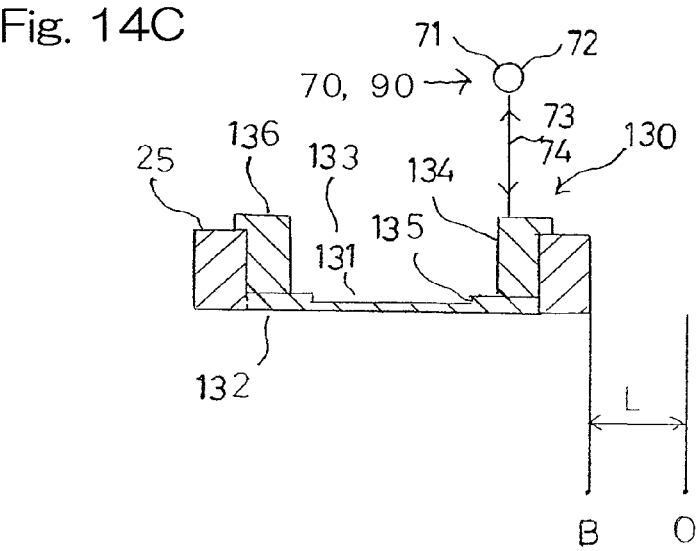
FIG. 14C is a schematic diagram showing the sample holder employed in the X-ray analyzing apparatus shown in FIG. 13A when the radially oriented end of the insertion hole is detected.

As shown in FIG. 14C, the sample holder identifying section 35 moves the sample stage 25, having placed thereon the sample holder 120 to which the sample S is not transported by the transport section 23, in a direction radially of the insertion hole 133 from the reference position O, while the laser beam 73 from the semiconductor laser 71 is projected, to the position A (shown in FIG. 14B), at which the spot changes from the spot position on the position sensitive detector 72 at the reference position O, that is, the position at which the laser beam 73 is projected onto the radially oriented end 135 of the recessed inlet 131 in the disc shaped pedestal, and further to the position B at which the spot changes from the spot position at the radially oriented end 135 of the recessed inlet 131, that is, the position at which the laser beam 73 is projected onto the radially oriented end 134 of the insertion hole 133, and then generates to the determining section 40 the sample holder identification signal for identifying the type of the sample holder 130 in dependence on the distance L of movement from the reference position O, with such identification signal retained subsequently.

In the next place, the sample holder identifying section 35 including the electric capacitance sensor assembly 90 for detecting the radially oriented end 135 of the recessed inlet will be described. As shown in FIG. 14A, the sample holder identifying section 35 moves the sample stage 25, having placed thereon the sample holder 120 to which the sample S is not transported by the transport section 23, from the reference position O in a direction radially of the recessed inlet 131 in the disc shaped pedestal. Then as shown in FIG. 14B, the sample stage 25 is moved to the position A, at which the detected electric capacitance of the electric capacitance sensor assembly 90 increases from the electric capacitance at the reference position O, that is, until the sample stage 25 is brought to a position immediately above the radially oriented end 135 of the recessed inlet 131, and the sample holder identification signal for identifying the type of the sample holder 130 in dependence on the distance L of movement from the reference position O is generated to the determining section 40, with the identification signal retained subsequently.

The sample holder identifying section 35 including the electric capacitance sensor assembly 90 for detecting the radially oriented end 134 of the insertion hole 133 in the sample holder 130 having the round recessed inlet 131 defied in the disc shaped pedestal 132 will now be described. As shown in FIG. 14C, the sample holder identifying section 35 moves the sample stage 25, having placed thereon the sample holder 130 to which the sample S is not transported by the transport section 23, in a direction radially of the insertion hole 133 from the reference position O, to the position A (shown in FIG. 14B), at which the detected electric capacitance of the electric capacitance sensor assembly 90 increases from the electric capacitance at the reference position O, that is, until the electric capacitance sensor assembly 90 is brought to a position immediately above the radially oriented end 135 of the recessed inlet 131 in the pedestal, and further to the position B, at which the detected electric capacitance of the electric capacitance sensor assembly 90 increases from the electric capacitance at the radially oriented end 135 of the recessed inlet 131, that is, until the electric static sensor assembly 90 is brought to a position immediately above the radially oriented end 134 of the insertion hole 133, and then generates to the determining section 40 the sample holder identification signal for identifying the type of the sample holder 130 in dependence on the distance L of movement from the reference position O, with such identification signal retained subsequently.

In the analyzing apparatus in which the sample holder identifying section 35 has the electric capacitance sensor assembly 90 and either one of the radially oriented end 135 of the recessed inlet 131 in the pedestal or the radially oriented end 134 of the insertion hole is detected, when the determining section 40 determines that the sample S and the sample holder 130 match with each other and the sample S is transported by the transport section 23 from the cassette 21 and is then placed in the sample holder 130, the sample holder identifying section 35 receives a signal indicative of the electric capacitance from the electric capacitance sensor assembly 90, that has changed from the electric capacitance at the reference position O. At this time, the sample holder identifying section 35 determines that the sample S has been placed in the sample holder 130 and then generates a signal indicative of the placement of the sample to the control section 50.

Since the apparatus according to the third embodiment is capable of automatically identifying the sample holder 8 in a manner similar to that performed by the apparatus according to the previously described first embodiment, functions and effects similar to those afforded by the apparatus according to the previously described first embodiment can be obtained.

The analyzing apparatus according to any one of the first to third embodiments of the present invention is provided with the following manual loading mode, as shown in FIGS. 6A and 6C, in which the analyst places the sample in the sample holder 8, 120, 130 that is placed on the sample stage 25 and performs the measurement by moving the sample stage 25 from a loading position to the measuring position.

At the outset, at step S1 shown in FIG. 6A, the analyst starts the operation of the apparatus. At subsequent step S2, the analyst sets the measuring conditions. Then at step S3, the analyst selects the manual loading mode (measurement by a manual feed). After the selection of the manual loading mode at step S3, the sample holder identifying section 35 determines at step M1 whether or not the sample S has been placed in the sample holder 8, 120, 130. If the sample S has not yet been placed, the flow goes to step M11 at which the display section 60 display a legend that the sample S has not yet been placed.

On the other hand, if at step M1 the placement of the sample S has been determined, the flow goes to step M2 at which the analyst presses a measurement initiating button. At subsequent step M3, the sample stage 25 having the sample S having been placed moves from the loading position to the measuring position. At step M4 following step M3, the measurement is initiated. Upon completion of the measurement, step M5 takes place at which the sample stage 25 is moved from the measuring position to the loading position.

Where the sample S is to be measured thereafter, the sample S has to be removed from the sample holder 8, 120, 130 and a sample S to be measured subsequently has then to be placed in the sample holder 8, 120, 130, followed by the steps in the manner described hereinabove. On the other hand, where there is no sample S to be measured thereafter, the analyst has to remove the sample S from the sample holder 8, 120, 130, followed by removal of the cassette at step S14 shown in FIG. 6C, thereby terminating the measurement at step S15.

Since in the analyzing apparatus according to any one of the first to third embodiments of the present invention the measurement can be performed with the sample S placed manually in the sample holder, the measurement can be carried out quickly in case of measurement of a small number of samples or measurement that is different from the routine analysis.

Although in the analyzing apparatus according to any one of the first to third embodiments of the present invention, the operation to identify the sample holder 8, 120, 130 has been described as performed with the lid 102 left opened, the operation to identify the sample holder 8, 120, 130 with the lid 102 closed may be performed.

In describing the analyzing apparatus according to any one of the first to third embodiments of the present invention, reference has been made to the wavelength dispersive X-ray fluorescence spectrometer of the upward irradiating and simultaneous multi-elements analyzing type, in which the fixed type goniometers are arranged to permit the multi-elements can be analyzed simultaneously. However, the analyzing apparatus of the present invention may be a wavelength dispersive X-ray fluorescence spectrometer in which a scanning type goniometer is arranged, or an energy dispersive X-ray fluorescence spectrometer. Also, it may be any X-ray analyzing apparatus of a type utilizing the sample holder of a structure on which the disc shaped sample S is placed such as the sample holder 8, 120 and 130 and may be, for example, a complex X-ray analyzing apparatus in which, for example, an X-ray fluorescence spectrometer, an X-ray reflectometer and an X-ray diffractometer are combined. In addition, it may be any other analyzing apparatus such as, for example, an EPMA for performing the analysis by radiating electron beams onto the sample, or an ellipsometer for performing the analysis by radiating luminous rays onto the sample.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

1 . . . X-ray source
2 . . . Primary X-rays
4 . . . Secondary X-rays
8, 120, 130 . . . Sample holder
20 . . . Cassette unit
21 . . . Cassette
22 . . . Cassette identifying section
23 . . . Transport section
25 . . . Sample stage
35 . . . Sample holder identifying section
40 . . . Determining section
82 . . . Ring shaped pedestal
83 . . . Insertion hole
84 . . . Radially oriented end of the insertion hole
85 . . . Radially inward end of the ring shaped pedestal
106 . . . Sample holder replacement door
S . . . Sample

What is claimed is:

1. An analyzing apparatus for analyzing a disc shaped sample, which comprises:

a cassette unit comprising a cassette for accommodating the sample and a cassette identifying section for identifying a type of the cassette and then generating a cassette identification signal descriptive of the diameter of the sample to be accommodated;

a sample holder having defined therein an insertion hole with a diameter, corresponding to the diameter of the sample, and through which the sample is inserted from above and including a ring shaped pedestal with an inner diameter, corrresponding to the diameter of the sample, and on which the sample is placed from above;

a transport section for transporting the sample from the cassette onto the sample holder;

a sample stage on which the sample holder is placed;

a sample holder identifying section for detecting a radially oriented end of the insertion hole in the sample holder or a radially inward end of the ring shaped pedestal and then generating a sample holder identification signal for identifying the type of the sample holder that corresponds to the diameter of the sample to be placed;

a determining section for determining whether or not the diameter of the sample to be accommodated in the cassette and the diameter of the sample to be placed on the pedestal of the sample holder match with each other, based on the cassette identification signal, generated from the cassette identifying section, and the sample holder identification signal generated from the sample holder identifying section; and a sample holder replacement door which is selectively opened or closed at the time of replacement of the sample holder, the sample holder retaining the sample holder identification signal when closed, but invalidating the sample holder identification signal when opened;

in which in the event that the determining section determines that the diameter of the sample to be accommodated in the cassette and the diameter of the sample to be placed on the pedestal of the sample holder match with each other, the transport section transports the sample from the cassette onto the sample holder placed on the sample stage.

2. The analyzing apparatus as claimed in claim 1, in which when the sample holder replacement door is closed, the sample holder identifying section identifies the type of the sample holder and then generates the sample holder identification signal.

3. The analyzing apparatus as claimed in claim 1, in which the sample holder replacement door is operated in the sequence in which the sampler holder replacement door is released from a locked condition by a lock release switch for unlocking a locking mechanism, opened by an analyst, invalidates the sample holder identification signal then retained, closed by the analyst, locked by the lock mechanism, and retains the sample holder identification signal generated by the sample holder identifying section.

4. The analyzing apparatus as claimed in claim 1, in which the sample holder identifying section comprises a non-contact type sensor assembly for detecting the radially oriented end of the insertion hole or the radially inward end of the ring shaped pedestal, the non-contact type sensor assembly being operable to detect the presence or absence of the sample within the sample holder placed on the sample stage and then generating a sample presence or absence signal.

5. The analyzing apparatus as claimed in claim 1, further comprising a manual loading mode in which an analyst places the sample in the sample holder then placed on the sample stage and then moves the sample stage from a loading position, which is a position where the sample is placed, to a measuring position, which is a position where the sample is measured, for measurement of the sample.

6. An analyzing apparatus for analyzing a disc shaped sample, which comprises:

a cassette unit comprising a cassette for accommodating the sample and a cassette identifying section for identifying a type of the cassette and then generating a cassette identification signal descriptive of the diameter of the sample to be accommodated;

a sample holder having defined therein an insertion hole with a diameter, corresponding to the diameter of the sample, and through which the sample is inserted from above and including a disc shaped pedestal on which the sample is placed;

a transport section for transporting the sample from the cassette onto the sample holder;

a sample stage on which the sample holder is placed;

a sample holder identifying section for detecting a radially oriented end of the insertion hole in the sample holder and then generating a sample holder identification signal for identifying the type of the sample holder that corresponds to the diameter of the sample to be placed;

a determining section for determining whether or not the diameter of the sample to be accommodated in the cassette and the diameter of the sample to be placed on the pedestal of the sample holder match with each other, based on the cassette identification signal, generated from the cassette identifying section, and the sample holder identification signal generated from the sample holder identifying section; and a sample holder replacement door which is selectively opened or closed at the time of replacement of the sample holder, the sample holder retaining the sample holder identification signal when closed, but invalidating the sample holder identification signal when opened;

in which in the event that the determining section determines that the diameter of the sample to be accommodated in the cassette and the diameter of the sample to be placed on the pedestal of the sample holder match with each other, the transport section transports the sample from the cassette onto the sample holder placed on the sample stage.

7. The analyzing apparatus as claimed in claim 6, in which the sample holder has a recessed inlet of a round configuration, with a diameter, corresponding to the diameter of the sample, defined in the disc shaped pedestal and in which the sample holder identifying section detects a radially oriented end of the insertion hole in the sample holder or a radially oriented end of the recessed inlet and then generates the sample holder identification signal for identifying the type of the sample holder that corresponds to the diameter of the sample to be placed.

8. The analyzing apparatus as claimed in claim 6, in which when the sample holder replacement door is closed, the sample holder identifying section identifies the type of the sample holder and then generates the sample holder identification signal.

9. The analyzing apparatus as claimed in claim 6, in which the sample holder replacement door is operated in the sequence in which the sampler holder replacement door is released from a locked condition by a lock release switch for unlocking a locking mechanism, opened by an analyst, invalidates the sample holder identification signal then retained, closed by the analyst, locked by the lock mechanism, and retains the sample holder identification signal generated by the sample holder identifying section.

10. The analyzing apparatus as claimed in claim 6, in which the sample holder identifying section comprises a non-contact type sensor assembly for detecting the radially oriented end of the insertion hole, the non-contact type sensor assembly being operable to detect the presence or absence of the sample within the sample holder placed on the sample stage and then generating a sample presence or absence signal.

11. The analyzing apparatus as claimed in claim 7, in which the sample holder identifying section comprises a non-contact type sensor assembly for detecting the radially oriented end of the insertion hole or the radially oriented end of the recessed inlet, the non-contact type sensor assembly being operable to detect the presence or absence of the sample within the sample holder placed on the sample stage and then generating a sample presence or absence signal.

12. The analyzing apparatus as claimed in claim 6, further comprising a manual loading mode in which an analyst places the sample in the sample holder then placed on the sample stage and then moves the sample stage from a loading position, which is a position where the sample is placed, to a measuring position, which is a position where the sample is measured, for measurement of the sample.

* * * * *